United States Patent
Wojciechowski et al.

(10) Patent No.: US 8,383,397 B2
(45) Date of Patent: Feb. 26, 2013

(54) METHOD AND SYSTEM FOR THE PRODUCTION OF CELLS AND CELL PRODUCTS AND APPLICATIONS THEREOF

(75) Inventors: Robert J. Wojciechowski, Forest Lake, MN (US); Darrell P. Page, East Bethal, MN (US); Karl P. Bongers, Coon Rapids, MN (US); Scott T. Waniger, Andover, MN (US); Beverly Norris, Blaine, MN (US); Mark D. Hirschel, Blaine, MN (US); Thiem Chan Duong Wong, Brooklyn Park, MN (US); Martin P. Crep, St. Paul, MN (US); Michael J. Gramer, Lino Lakes, MN (US); Grant Adams, Coon Rapids, MN (US)

(73) Assignee: Biovest International, Inc., Minneapolis, MN (US)

( * ) Notice: Subject to any disclaimer, the term of this patent is extended or adjusted under 35 U.S.C. 154(b) by 890 days.

(21) Appl. No.: 12/274,993

(22) Filed: Nov. 20, 2008

(65) Prior Publication Data
US 2009/0269841 A1   Oct. 29, 2009

Related U.S. Application Data

(63) Continuation-in-part of application No. PCT/US2007/012042, filed on May 21, 2007, and a continuation-in-part of application No. PCT/US2007/012051, filed on May 21, 2007, and a continuation-in-part of application No.
(Continued)

(51) Int. Cl.
   *C12M 1/00* (2006.01)

(52) U.S. Cl. .................... 435/289.1; 435/303.1; 417/474

(58) Field of Classification Search .............. 435/289.1, 435/303.1, 325; 438/76, 138; 257/216; 417/474, 417/475
See application file for complete search history.

(56) References Cited

U.S. PATENT DOCUMENTS
3,148,624 A   9/1964   Baldwin
(Continued)

FOREIGN PATENT DOCUMENTS
EP   0164020 B1   8/1989
EP   1400691 A2   3/2004
(Continued)

OTHER PUBLICATIONS

International Search Report dated Oct. 4, 2007 for International Patent Application No. PCT/US2007/012042, filed May 21, 2007, 2 pages.
(Continued)

*Primary Examiner* — Michael Hobbs
(74) *Attorney, Agent, or Firm* — Saliwanchik, Lloyd & Eisenschenk

(57) ABSTRACT

A cell culture system for the production of cells and cell derived products includes a reusable instrumentation base device incorporating hardware to support cell culture growth. A disposable cultureware module including a cell growth chamber is removably attachable to the instrumentation base device. The base device includes microprocessor control and a pump for circulating cell culture medium through the cell growth chamber. The cultureware module is removably attached to the instrumentation base device. Cells are introduced into the cell growth chamber and a source of medium is fluidly attached to the cultureware module. Operating parameters are programmed into the microprocessor control. The pump is operated to circulate the medium through the cell growth chamber to grow cells or cell products therein. The grown cells or cell products are harvested from the cell growth chamber and the cultureware module is then disposed.

17 Claims, 31 Drawing Sheets

Related U.S. Application Data

PCT/US2007/102052, filed on May 21, 2007, and a continuation-in-part of application No. PCT/US2007/012053, filed on May 21, 2007, and a continuation-in-part of application No. PCT/US2007/012054, filed on May 21, 2007.

(60) Provisional application No. 60/802,376, filed on May 22, 2006.

(56) References Cited

U.S. PATENT DOCUMENTS

| | | | |
|---|---|---|---|
| 4,282,902 A | | 8/1981 | Haynes |
| 4,417,861 A | | 11/1983 | Tolbert |
| 4,604,038 A | | 8/1986 | Belew |
| 4,804,628 A | | 2/1989 | Cracauer et al. |
| 5,113,906 A | | 5/1992 | Högner |
| 5,318,413 A | * | 6/1994 | Bertoncini ............ 417/475 |
| 5,622,857 A | * | 4/1997 | Goffe ............ 435/378 |
| 5,958,763 A | * | 9/1999 | Goffe ............ 435/303.1 |
| 2003/0040104 A1 | * | 2/2003 | Barbera-Guillem ....... 435/286.2 |
| 2004/0057856 A1 | | 3/2004 | Saxer et al. |
| 2007/0062872 A1 | * | 3/2007 | Parker et al. ............ 210/650 |
| 2007/0148010 A1 | | 6/2007 | Michels et al. |
| 2009/0215022 A1 | | 8/2009 | Page et al. |

FOREIGN PATENT DOCUMENTS

| | | |
|---|---|---|
| WO | WO 02/087662 A1 | 11/2002 |
| WO | WO 03/087292 A2 | 10/2003 |
| WO | WO 2005/031167 A1 | 4/2005 |
| WO | WO 2005/116186 A1 | 12/2005 |
| WO | WO 2007/136821 A1 | 11/2007 |
| WO | WO 2007/139742 A1 | 12/2007 |
| WO | WO 2007/139746 A1 | 12/2007 |
| WO | WO 2007/139747 A1 | 12/2007 |
| WO | WO 2007/139748 A2 | 12/2007 |

OTHER PUBLICATIONS

International Search Report dated Oct. 5, 2007 for International Patent Application No. PCT/US2007/012051, filed May 21, 2007, 2 pages.

International Search Report dated Oct. 4, 2007 for International Patent Application No. PCT/US2007/012052, filed May 21, 2007, 2 pages.

International Search Report dated Nov. 7, 2007 for International Patent Application No. PCT/US2007/012053, filed May 21, 2007, 2 pages.

International Search Report dated Sep. 25, 2007 for International Patent Application No. PCT/US2007/012054, filed May 21, 2007, 3 pages.

* cited by examiner

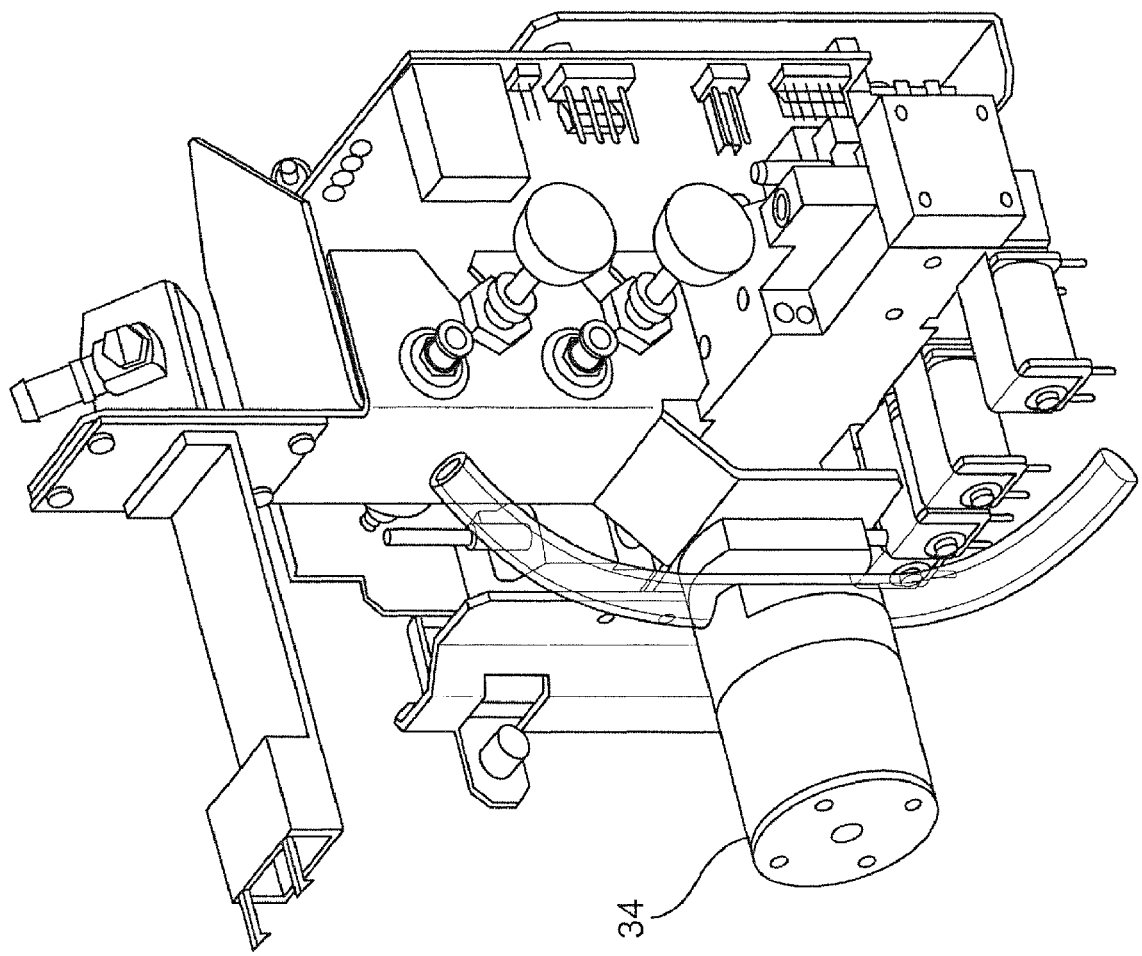

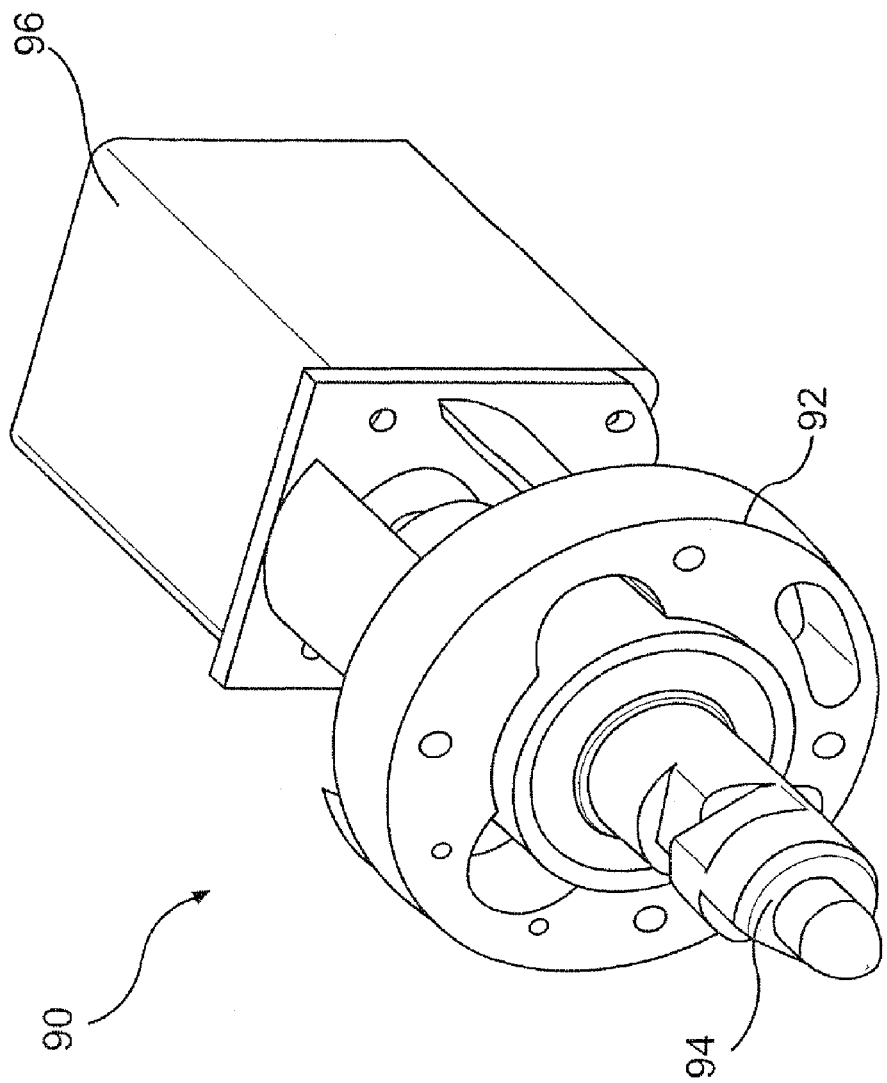

| | | PH | GAS | ICP | ECP | ECS | REF.T | MED.T | INC.T | OUT | MED | FACT | HARV | CIRC |
|---|---|---|---|---|---|---|---|---|---|---|---|---|---|---|
| OCT. 01, 2004 9:47.43 | AIR INLET PRESSURE LOW | | | | | | | | | | | | | |
| OCT. 01, 2004 9:47.43 | | 6.65 | 0.0 | 0 | 0 | FALL | 1.6 | 25.0 | 26.1 | 0 | 100 | 0 | 0 | 200 |
| OCT. 01, 2004 9:47.49 | FALL CYCLE COMPLETE IN 0:03 | | | | | | | | | | | | | |
| OCT. 01, 2004 9:48.26 | STARTUP, DOWN TIME: 0-00:00 | | | | | | | | | | | | | |
| OCT. 01, 2004 9:49.48 | RISE CYCLE COMPLETE IN 0:02 | | | | | | | | | | | | | |
| OCT. 01, 2004 9:52.44 | | 7.10 | 50.8 | 0 | 51 | FALL | 5.2 | 38.1 | 48.7 | 125 | 100 | 0 | 0 | 200 |
| OCT. 01, 2004 9:54.53 | FALL CYCLE COMPLETE IN 5:05 | | | | | | | | | | | | | |
| OCT. 01, 2004 9:55.29 | RISE CYCLE COMPLETE IN 0:36 | | | | | | | | | | | | | |
| OCT. 01, 2004 9:57.45 | | 7.10 | 49.8 | 0 | 51 | FALL | 5.0 | 37.4 | 48.7 | 125 | 100 | 0 | 0 | 200 |
| OCT. 01, 2004 9:58.59 | INSTRUMENT HOLD, PUMPS STOPPED | | | | | | | | | | | | | |
| OCT. 01, 2004 9:59.00 | INSTRUMENT RESUMED FROM HOLD | | | | | | | | | | | | | |

TOTAL: 278     RECORDS 158 THRU 168     FREE: 0.0 MB

[TOP] [PG UP] [◁] [▷] [PG DN] [END]

[HOLD] [EXIT] [HELP]

METHOD AND SYSTEM FOR THE PRODUCTION OF CELLS AND CELL PRODUCTS AND APPLICATIONS THEREOF

CROSS-REFERENCE TO RELATED APPLICATIONS

This application is a continuation-in-part of: International Application No. PCT/US2007/012042, filed May 21, 2007, which claims the benefit under 35 USC §119 of U.S. Application No. 60/802,376, filed May 22, 2006, both of which are incorporated herein by reference in their entirety;

International Application No. PCT/US2007/012051, filed May 21, 2007, which claims the benefit of U.S. Application No. 60/802,376, filed May 22, 2006, both of which are incorporated herein by reference in their entirety;

International Application No. PCT/US2007/012052, filed May 21, 2007, which claims the benefit of U.S. Application No. 60/802,376, filed May 22, 2006, both of which are incorporated herein by reference in their entirety;

International Application No. PCT/US2007/012053, filed May 21, 2007, which claims the benefit of U.S. Application No. 60/802,376, filed May 22, 2006, both of which are incorporated herein by reference in their entirety; and International Application No. PCT/US2007/012054, filed May 21, 2007, which claims the benefit of U.S. Application No. 60/802,376, filed May 22, 2006; both of which are incorporated herein by reference in their entirety.

BACKGROUND OF THE INVENTION

1. Field of the Invention

The present invention relates to a method and system that creates a self-contained culture environment, and more particularly to a cell culture system incorporating a disposable cultureware module and a reusable compact instrumentation base device that is capable of expanding cells including primary cells and cell lines as well as patient-specific cells or cells lines in an automated, contaminant-free manner.

2. Description of the Related Art

The anticipated growth of personalized medicine will require new paradigms for the manufacture of therapies tailored to the needs of individual patients. The greatest challenge is expected to come in the area of cell based therapies, especially when such therapies are autologous in nature. In such cases each cell or cell based product will need to be manufactured from scratch for each patient. Manual methods for mammalian cell culture, by their nature, are prone to technician error or inconsistency leading to differences between supposed identical cultures. This becomes especially evident as more and more autologous cells are expanded for personalized therapies. Patient-specific cells, or proteins, are subject to variation, especially when scaled beyond levels that can be managed efficiently with manual methods.

In addition to being labor intensive, the stringent requirements for segregation of each patient's materials from that of every other patient will mean that manufacturing facilities will be large and complex, containing a multitude of isolation suites each with its own equipment (incubators, tissue culture hoods, centrifuges) that can be used for only one patient at a time. Because each patient's therapy is a new and unique product, patient specific manufacturing will also be labor intensive, requiring not just direct manufacturing personnel but also disproportionately increased manpower for quality assurance and quality control functions.

Moreover, conventional approaches and tools for manufacturing cells or cell based products typically involve numerous manual manipulations that are subject to variations even when conducted by skilled technicians. When used at the scale needed to manufacture hundreds or thousands of different cells, cell lines and patient specific cell based therapies, the variability, error or contamination rate may become unacceptable for commercial processes.

Small quantities of secreted product are produced in a number of different ways. T-flasks, roller bottles, stirred bottles or cell bags are manual methods using incubators or warm-rooms to provide environments for cell growth and production. These methods are very labor intensive, subject to mistakes and difficult for large scale production.

Another method, ascites production, uses a host animal (usually a mouse) where the peritoneum is injected with the cells that express the product and are parasitically grown and maintained. The animals are sacrificed and the peritoneal fluid with the product is collected. This method is also very labor intensive, difficult for large scale production and objectionable because of the use of animals. Another method is to inoculate and grow the cells in a small stirred tank or bioreactor or bag-type chamber. The tank provides the environmental and metabolic needs and the cell secretions are allowed to accumulate. This method is costly in terms of facility support in order to do a large number of unique cells and produces product at low concentration.

Another method is to use a bioreactor (hollow fiber, ceramic matrix, fluidizer bed, etc) in lieu of the stirred tank. This can bring facilities costs down and increases product concentration. Biovest International of Coon Rapids, Minn., has or had instruments using these technologies—hollow fiber, ceramic matrix, fluidized bed and stirred tanks.

Cell culturing devices or cultureware for culturing cells in vitro are known. As disclosed in U.S. Pat. No. 4,804,628, the entirety of which is hereby incorporated by reference, a hollow fiber culture device includes a plurality of hollow fiber membranes. Medium containing oxygen, nutrients, and other chemical stimuli is transported through the lumen of the hollow fiber membranes or capillaries and diffuses through the walls thereof into an extracapillary (EC) space between the membranes and the shell of the cartridge containing the hollow fibers. The cells that are to be maintained collect in the extracapillary space. Metabolic wastes are removed from the bioreactor. The cells or cell products can be harvested from the device.

Known EC reservoirs have typically been rigid. They are a pressure vessel and therefore require a sealed compartment with tubing ports adding to costs. A gas, typically air, is introduced through a sterile barrier, generally a membrane filter, to control pressure in the vessel. Fluid level control has been limited to ultrasonic, conductive or optical trip points, or by a load cell measuring the weight of the fluid. Reservoirs are expensive and difficult to manufacture. There is limited EC fluid level measurement accuracy-ultrasonic, conductive or optical monitoring of fluid levels are commonly fouled by cell debris in the reservoir. Alternatively, load cells are not a rugged design for reliable fluid level sensing.

Another problem with the prior art systems is the inability to control lactate and sense pH in the system. One prior art method takes samples of the culture medium and analyzes it using an off-line analyzer. The operator adjusts the perfusion medium rate based on values obtained to maintain the lactate concentration at the level desired. The operator must attempt to predict future lactate levels when adjusting media feed rates. This is labor intensive, presents potential breech of sterility, and the level of lactate control accuracy is dependent on operator skill.

Another method is to connect an automated sampler/analyzer to periodically withdraw sample of the culture media, analyze it and provide feedback for a media feed controller. This method requires additional equipment and increases the risk of sterility breech.

Yet another method is to use an invasive lactate sensor to directly read the lactate level and provide feedback for a media feed controller. In line lactate sensors need to be sterilizable, biocompatible, typically have low reliability and need periodic maintenance.

These methodologies rely on costly, labor intensive off-line sampling and analysis or additional equipment to interface with the instrument or require the addition of a lactate probe and electronics to the culture.

Disposable cultureware generally cannot be autoclaved, so a pH sensor is historically sterilized separately and then added to the cultureware. However, adding the probe risks compromising the sterility of the cultureware. Probe addition is performed in a sterile environment (laminar flow hood) and increases the manpower needed.

The previous methodologies that utilize off-line sampling are subject to contamination problems and depend on the skill of the operator in predicting future lactate levels and influence of media dilution rate. Sampling equipment need interfacing to the culture fluidic circuit, an interface for the feedback signal and periodic calibration of the probes used for sampling. The lactate probe requires interface with the fluid circuit, a method for sterilization or a sterile barrier, interface electronics to convert the probe signal to a useful feedback and a method to calibrate in the fluid circuit.

Preparing the system to start the cell culture is also very labor intensive. The cultureware must be assembled and sterilized or probes must be prepared, sterilized and aseptically inserted into the pre-sterilized portion of the cultureware. The cultureware assembly is then loaded onto the instrument. A series of manual operations are needed to check the integrity of the assembly, introduce fluid into the cultureware flow path, flush the toxic residuals (e.g. surfactants) from the cultureware, start the cultureware in a pre-inoculation mode, introduce factors into the flow path getting it ready for the cells, inoculating the cells into the bioreactor and starting the run (growth of the cell mass and eventual harvest of product).

Two methods are generally used for sterilization. One method places an electrode in a holder, steam sterilizes the assembly (probe) and then aseptically inserts the probe into the pre-sterilized cultureware. The second method involves placing a non-sterile probe into a holder and then using steam to sterilize the electrode in place, referred to as steam in place. Both methods are labor intensive, prone to failure and the procedures need to be validated.

Other methods exist which are less common. Cold sterilants can be used to sterilize the holder and electrode before aseptic insertion. A permeable membrane can be used to isolate the non-sterile probe from the sterile fluid being sensed. A holder with the membrane is placed in the fluid path, either before sterilization or after if the holder and membrane is sterilized separately, and then the sensor is placed against or close to the membrane and the fluid on both sides of the membrane is assumed to be equilibrated.

Glass electrodes have not been included with the cultureware in the past because it was unknown if the probes could survive EtO sterilization and being stored dry. Filled glass electrodes are normally stored hydrated in a liquid buffer.

Each unique cell or cell line must be cultured, cell products harvested and purified separately. In order to do a large number of unique cells or cell lines, a considerable number of instruments would be needed. If application of the cells or products for therapeutic purposes is contemplated strict segregation of each cell production process would be required. Consequently, compactness of the design and the amount of ancillary support resources needed will become an important facilities issue. Moreover the systems currently available are general purpose in nature and require considerable time from trained operators to setup, load, flush, inoculate, run, harvest and unload. Each step usually requires manual documentation.

Moreover, production tracking mandates generation of a batch record for each cell culture run. Historically this is done with a paper-based system and relies on the operator inputting the information. This is labor intensive and subject to errors.

Current purification techniques also involve cleaning and reuse of components. This requires Standard Operational Procedures (SOPs) to be written and the cleaning and reuse process to be validated. This is a time intensive activity.

Accordingly, there is a need for a system and method whereby cells and/or cell products can be cultured in a fully automated, rapid and sterile manner.

SUMMARY OF THE INVENTION

One aspect of the present invention is to provide a modular and integrated system for the production and expansion of cells or cell lines. The system consists of a reusable control module housing with all of the mechanical and electronic components and disposable cell growth modules that attach to the control module. This system minimizes the need for skilled technicians and more importantly, prevents the possibility of cross-contamination in a multi-use facility. As an enclosed system, the safety provided by complete segregation facilitates direct applicability to therapies or diagnoses that require autologous cell culture. This self-contained, automated cell culture device allows for simultaneously culture of numerous cell cultures within a compact facility, without the need for individual, segregated cell culture suites. The system of the present invention provides a compact sealed containment system that will enable the cost effective manufacture of cells, cell lines, patient specific cells and cell products on an industrial scale.

Another aspect of the present invention is to provide a method and system that incorporates disposable cultureware, which eliminates the need for cleaning and reuse.

Yet another aspect of the present invention is a system that has the stand-alone integration of a large system in a bench top device (pumps, controls, incubator, refrigerator, cultureware, etc).

Still another aspect of the present invention is a system that incorporates a barcode reader and data gathering software that, when used with an information management system (such as a manufacturing execution system or MIMS), allows for automating generation of the batch record.

Another aspect of the present invention is to provide an EC cycling unit that costs less than rigid reservoirs. Moreover, due to the sealed EC circuit design, without vented reservoir, the chance of cell contamination is minimized.

Still another aspect of the present invention is to provide a system that controls lactate concentration in a perfusion cell culture system using measurement of $CO_2$ and pH.

Yet another aspect of the present invention is to eliminate preparation, autoclaving, and insertion of pH electrodes aseptically in the cultureware which requires a significant amount of time and may breach the sterile barrier of the cultureware set.

The system of the present invention incorporates features that greatly reduce the operator's time needed to support the operations (e.g. integrated pump cassette, pre-sterilized cultureware with pH sensors, quick-load cultureware) and designed automated procedures and apparatuses which allow the system to sequence through the operations (e.g. automated fluid clamps, control software).

The system is capable of integrating the cell culture product production and purification process. The design of the cultureware and instrument simplifies and reduces labor needed to produce product. This reduces sources of error in the process.

The present invention provides an automated cell culture system and method which creates a self-contained culture environment. The apparatus incorporates perfusion culture with sealed, pre-sterilized disposable cultureware, such as hollow fiber or other bioreactors, programmable process control, automated fluid valving, pH feedback control, lactic acid feedback control, temperature control, nutrient delivery control, waste removal, gas exchange mechanism, reservoirs, tubing, pumps and harvest vessels. Accordingly, the present cell culture apparatus (referred to as AutovaxID Cell Culture Module™) is capable of expanding cells in a highly controlled, contaminant-free manner. Cells to which this approach are applicable include transformed or non-transformed cell lines, primary cells including somatic cells such as lymphocytes or other immune cells, chondrocytes, myocytes or myoblasts, epithelial cells and patient specific cells, primary or otherwise. Included also are cells or cell lines that have been genetically modified, such as both adult and embryonic stem cells. Specifically, the automated cell culture apparatus allows for production and harvest of cells or cell-secreted protein in a manner that minimizes the need for operator intervention and minimizes the need for segregated clean rooms for the growth and manipulation of the cells. Further, the apparatus provides a culture environment that is completely self-contained and disposable. This eliminates the need for individual clean rooms typically required in a regulated, multi-use facility. Control of fluid dynamics within the bioreactor allows for growth conditions to be adjusted, e.g. changing growth factor concentrations, to facilitate application of unique culture protocols or expansion of unique cells or cell lines. As a result, there is less variation and less labor required for consistent, reproducible production of cells for applications to expansion of autologous cells and their use in personalized medicine applications.

According to these and other aspects of the present invention, there is provided a cell culture system for the production of cells and cell derived products including a reusable instrumentation base device incorporating hardware to support cell culture growth. A disposable cultureware module including a cell growth chamber is removably attachable to the instrumentation base device.

According to these and other aspects of the present invention, there is also provided a method for the production of cells and cell products in a highly controlled, contaminant-free environment comprising the steps of providing a disposable cultureware module including a cell growth chamber, and a reusable instrumentation base device incorporating hardware to support cell culture growth. The base device includes microprocessor control and a pump for circulating media through the cell growth chamber. The cultureware module is removably attached to the instrumentation base device. Cells are introduced into the cell growth chamber. A source of media is fluidly attached to the cultureware module. Operating parameters are programmed into the microprocessor control. The pump is operated to circulate the media through the cell growth chamber to grow cells or cell products therein. The grown cells or cell products are harvested from the cell growth chamber. The cultureware module is then disposed.

These and other features, aspects, and advantages of the present invention will become more apparent from the following detailed description of the preferred embodiment relative to the accompanied drawings, in which:

BRIEF DESCRIPTION OF THE DRAWINGS

FIG. 11 is a perspective view of the gas blending and fluid cycling control of the module of the present invention.

FIG. 13 is a perspective view of a rotary selection valve drive of the present invention.

FIGS. 26-31 are views of the touch screen associated with the automatic control of the system of the present invention.

DETAILED DESCRIPTION OF THE PREFERRED EMBODIMENTS

Figure 1:
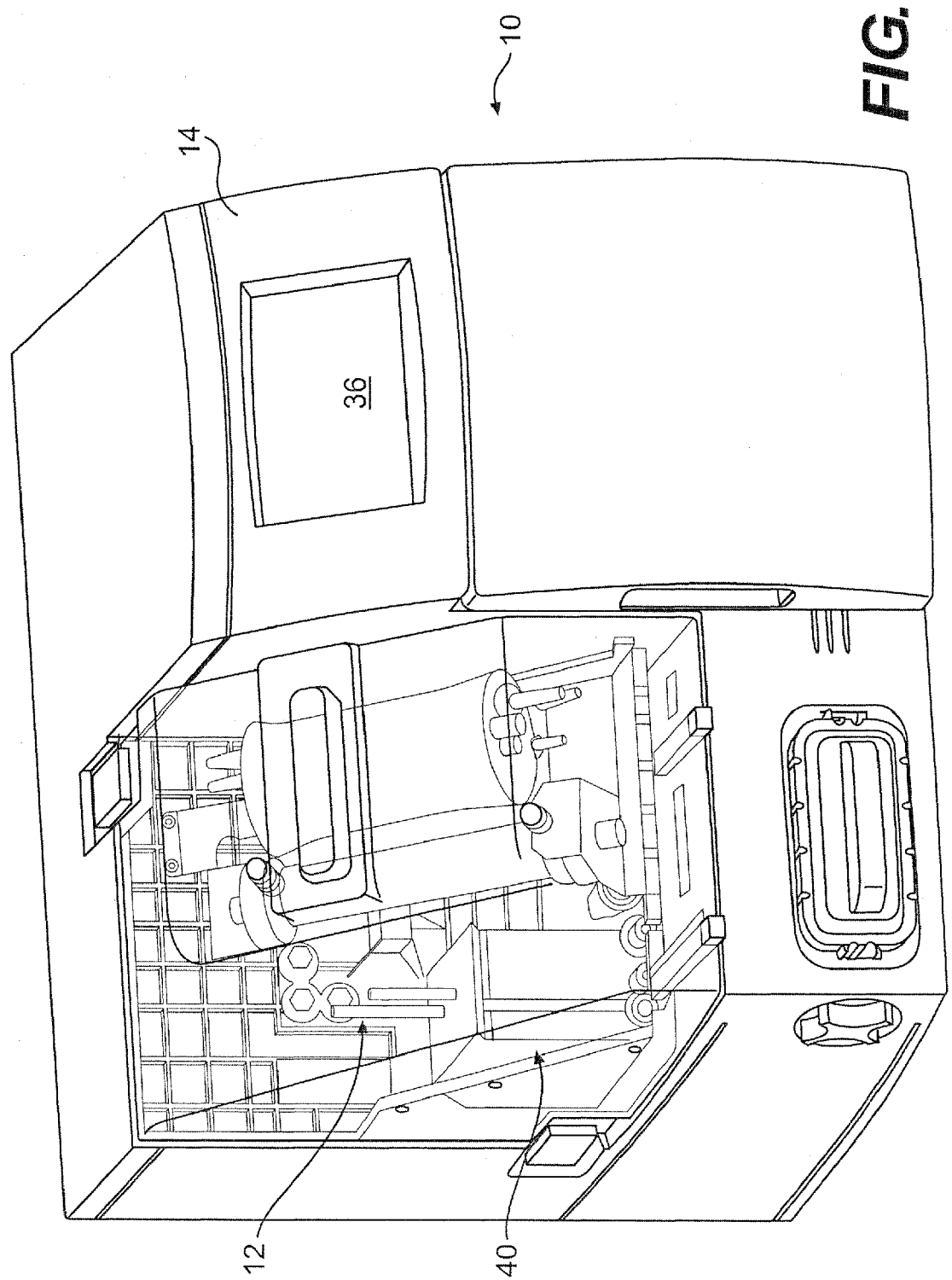
FIG. 1 is a perspective view of the system for producing cells and/or cell derived products according to the present invention.

Referring to FIG. 1, the present invention provides a fully integrated system 10 for producing cells and cell derived products in a closed, self-sufficient environment. More specifically, the system allows for cell expansion and harvest of cells and their products with minimal need for technician interaction. As will be described further herein, the device incorporates cell culture technology, for example, hollow fiber or similar bioreactor perfusion technology, with all tubing components other than the media feed, harvest tubing and tubes threaded through the pump cassette, encased in a single-use, disposable incubator 12. Following bioreactor inoculation with cells, the system follows pre-programmed processes to deliver media, maintain pH, maintain lactate levels, control temperature and harvest cells or cell-secreted protein. Standard or unique cell culture growth parameters can be programmed prior to bioreactor inoculation, such that, various cell types can be expanded and such that cells or cell products can be harvested in an efficient, reproducible manner with minimal chance of human error.

The system is based on cell growth chamber technology. For example, bioreactors that have a plurality of semi-permeable hollow fibers or other type of semi-permeable membrane or substrate potted in a housing to create a space inside the fiber or one side of the membrane (referred to as intracapillary or IC space) separate from that outside the fibers or on the other side of the membrane (referred to as extracapillary or EC space). Fluid distribution between the IC and EC space occurs through the fiber pores which can range in size from 10 MW(Kd) to 0.2 µm. Cells are placed on one side of the fiber or membrane, usually in the EC space, in a complete cell culture medium, which is usually the same medium used to expand cells prior to bioreactor inoculation (serum containing, serum-free, or protein-free medium). Cells are usually placed in the EC space when secreted protein is the desired product. In some instances, when cells are the desired product, it may be beneficial to place cells in the IC space.

Medium is perfused through a bioreactor 20 by circulating through the IC space at a fast rate. The medium can be a liquid containing a well-defined mixture of salts, amino acids, and vitamins that often contains one or more protein growth factors. This serves to deliver nutrients to the cell space and conversely, removes or prevents a toxic build-up of metabolic waste. During this circulation, medium is passed through an oxygenator or gas exchanger cartridge 24 which serves to provide pH control and oxygen for the cells and conversely, remove carbon dioxide from the culture. When the bioreactor 20 contains a smaller number of cells, just after inoculation, the oxygenator or gas exchange cartridge is used to provide $CO_2$ and subsequently control pH of the culture environment. As cell number increases, the oxygenator is used to remove $CO_2$ which serves to enhance acid neutralization and control the pH of the culture. Other bioreactor configurations, in addition to hollow fibers, that are designed and optimized for the growth and production of cells and production of cell-derived products are also included.

The system 10 provides significant efficiencies and cost reduction through its disposable component and enclosed operation. As such, cell lines are contained in a closed system and continuously cultured without the need for specialized, segregated clean rooms. This fully integrated apparatus eliminates the need for cleaning and sterilization validations, as well as the need for hard plumbing associated with conventional cell culture facilities.

Figure 2:
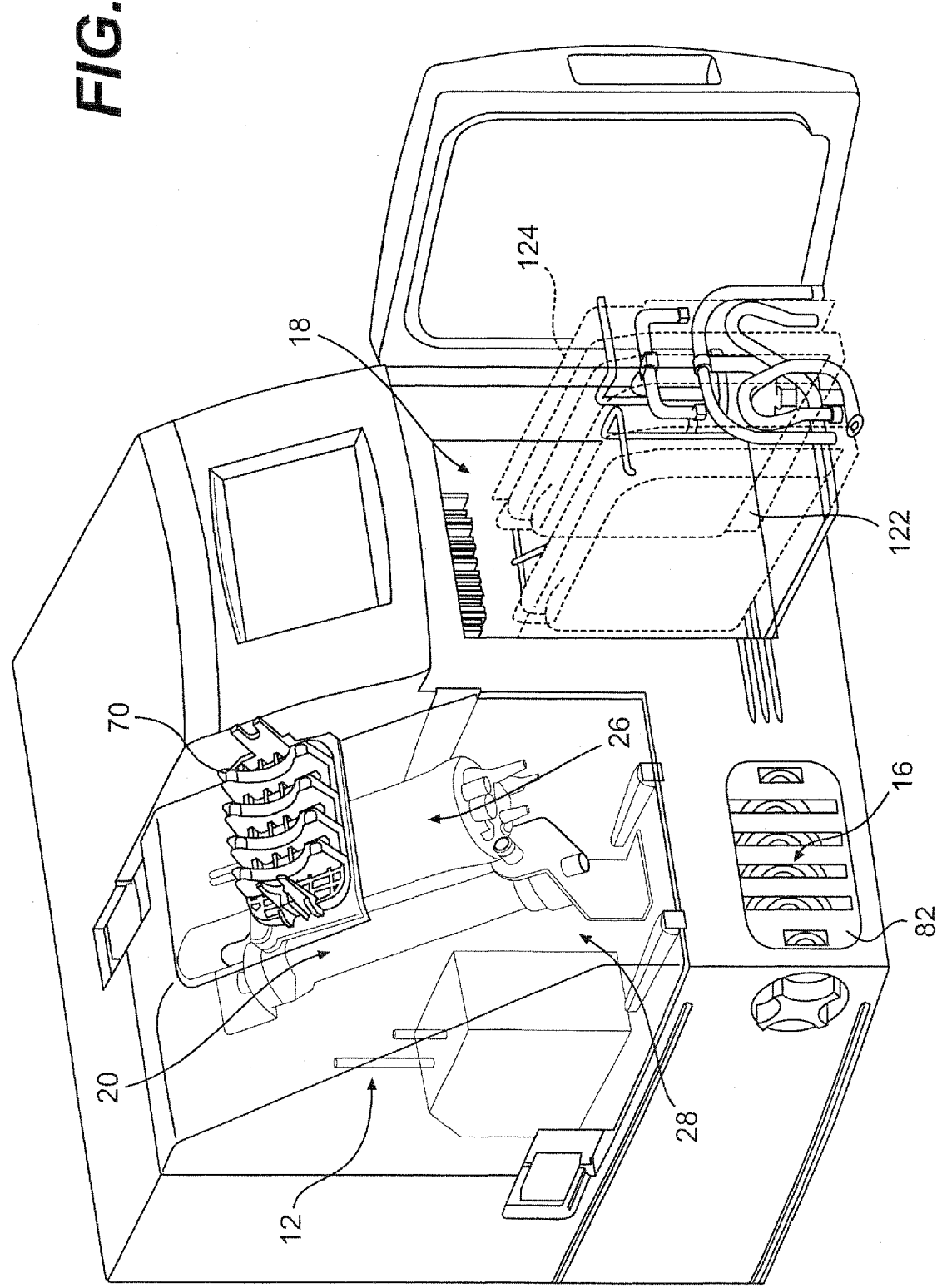
FIG. 2 is another perspective view of the system of the present invention.
Figure 5:
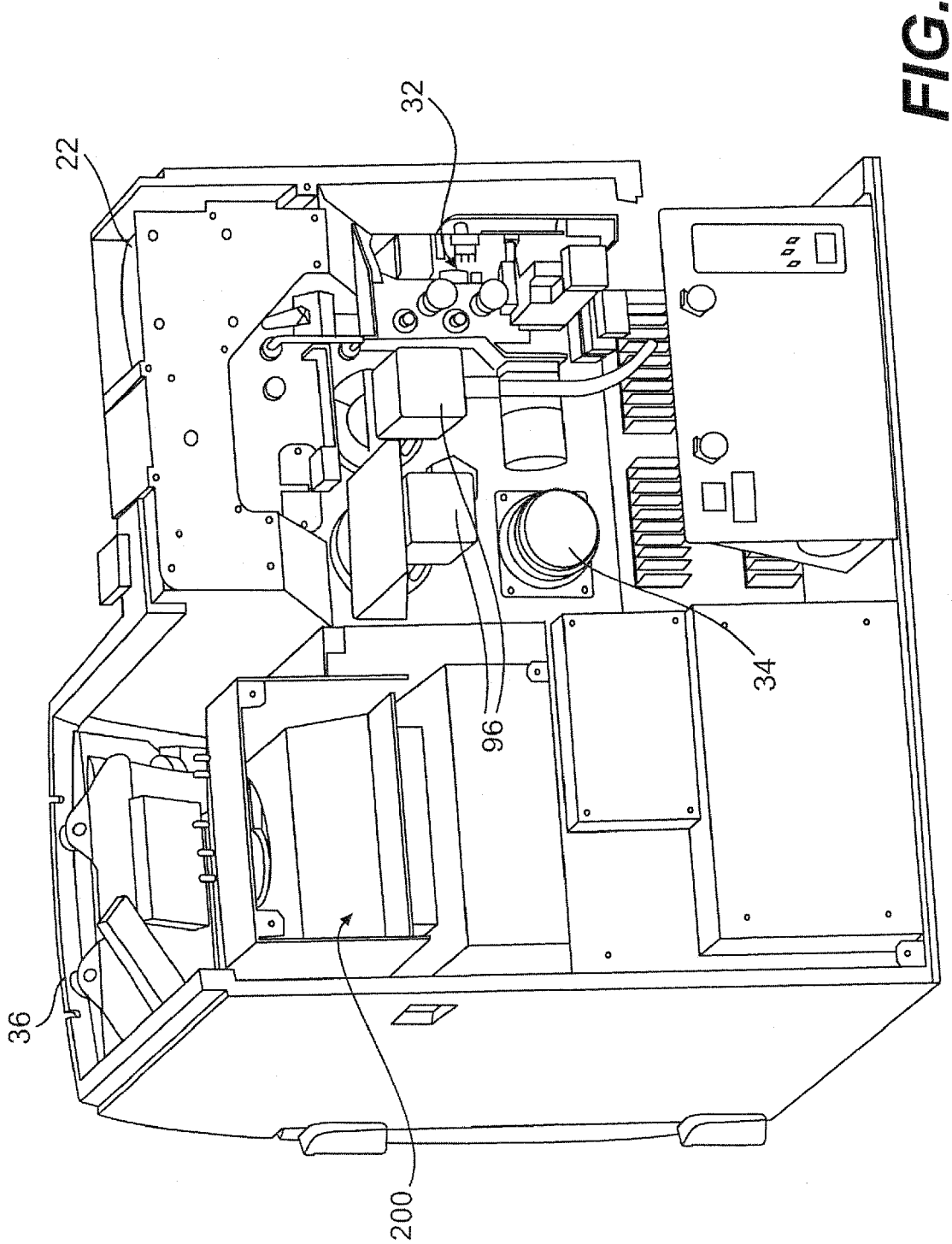
FIG. 5 is a rear view of the device with covers removed of FIG. 3.
Figure 6:
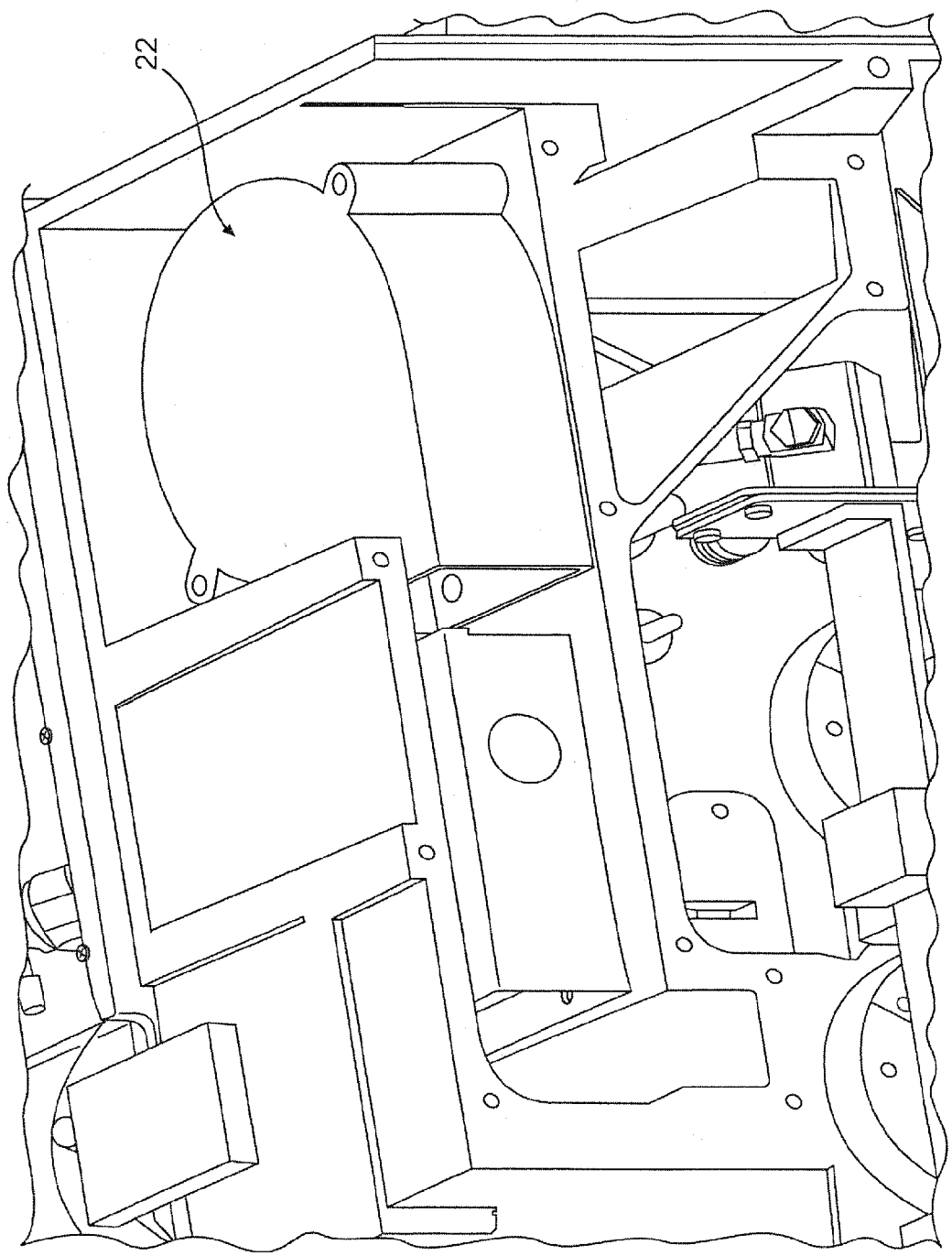
FIG. 6 is an enlarged view of the heating system of the device of FIG. 3.

Referring again to FIG. 1, the system consists of two individual parts: an instrumentation base device 14 that is reusable and an enclosed cultureware module 12 that is used for a single production run and is disposable. Numerous modules 12 can be used on a single device 14. The instrument provides the hardware to support cell culture growth and production in a compact package. As shown in FIG. 2, and as will be described in further detail herein, an easy-load multiple channel peristaltic pump drive 16 located in base device 14 and a pump cassette 70 move fresh basal media into the cultureware, removes spent media, adds growth factors or other supplements and removes product harvest. An integrated cool storage area 18 maintains the factor and harvest at a low temperature (approximately 4° C.). An integrated heating mechanism 22 (FIG. 6) maintains the cell environment to promote growth and production. Gas exchange cartridge 24 (FIG. 5), in conjunction with a cultureware pH sensor 26 controls the pH of the cell culture medium. Two automated tube valving drives 90 (FIG. 3) are used to control the cultureware flow path configuration to accomplish the fluidic switching functions needed to initiate and do a successful run. Valves 90 and sensors 32 (FIGS. 3, 5, 13) in the instrument control the fluid cycling in the cultureware module 12. A drive pump 34 (FIGS. 3, 5) for fluid circulation is provided. An attached barcode reader, not shown, facilitates operator and lot tracing. A communication port ties the instrument to a data information management system (such as a MES). A flat panel display 36 (FIG. 1) with touch screen is available for user interaction.

The one-time use cultureware module 12 is provided pre-sterilized. It is designed for quick loading onto the instrument ("quick-load"), as will be described further herein. The loading of the cultureware body makes connections to the instrument. Pump cassette 70 (FIG. 2), which is physically attached to the tubing, allows the user to quickly load the pump segments. This design and layout minimizes loading errors. The cultureware enclosure 12 provides an area that is heated to maintain cell fluid temperature. A fluid cycling unit 40 (FIGS. 1, 18) maintains fluid volumes and cycling and is included in the cultureware. Sensors for fluid circulation rate, pH and a thermal well for the instrument's temperature sensor are provided. The blended gas from the instrument is routed to gas exchange cartridge 24 that provides oxygen and adds or removes carbon dioxide to the circulated fluid to support cell metabolism. A magnetically coupled pump drive 34 (FIGS. 11-12) circulates fluid thru the bioreactor 20 and gas exchange cartridge 24. The bioreactor 20 that provides the cell space and media component exchange is also in the cultureware. Disposable containers for harvest collection are provided. Prior to the beginning of the culture the operator attaches a media source, factor bag and spent media container to the cultureware before running. At the conclusion of the run the harvest containers are removed or drained, media and spent media container is disconnected, pump cassette is unloaded, harvest bag disconnected, cultureware body is unloaded and the used cultureware is placed in a biohazard container for disposal.

Cell expansion and subsequent process tracking mandates generation of a batch record for each culture. Historically this is done with a paper-based system that relies on operator input of the information. This is labor intensive and subject to errors. The fully integrated device incorporates a barcode reader and data gathering software which, when used with the information management system (MES), allows for automatic generation of the batch record.

The system of the present invention has application in a regulated cell culture environment. It is anticipated that autologous whole cell therapies or patient-specific proteins (vaccines) therapies, would by their nature, require the simultaneous culture of numerous cell lines in a single facility. In addition to the segregation created through this closed culture approach, the apparatus is designed to support a standard information management system (such as a LIMS or MES) protocol. This capability contributes to the creation of thorough batch records and verification of culture conditions to ensure standardization, tracking and safety of each product. This capability facilitates the multi-product concept that is pivotal to facilities involved with autologous or patient-specific products.

Figure 10:
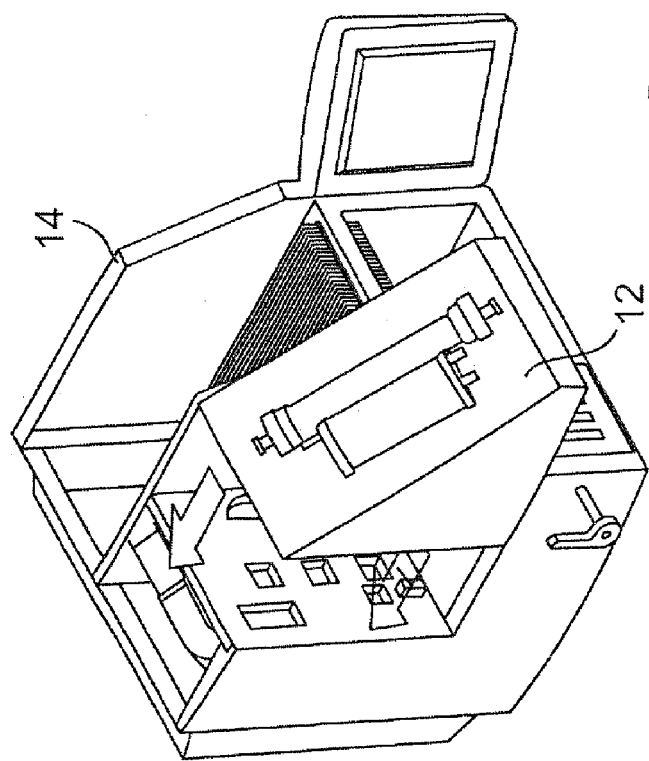
FIG. 10 illustrates the installation method of the cell culture module and the device of the present invention.

Referring to FIG. 1, disposable cell culture module 12 is removably attachable to device 14. The module requires multiple mechanical and electrical interfaces to the control instrumentation of device 14. Module 12 has interface features integrated into the module that mate with instrument interface features in the device to allow for a single motion installation (FIG. 10). As modules 12 are to be disposed of after use, it should be appreciated that numerous modules can be used in conjunction with a single base device 14.

Figure 3:
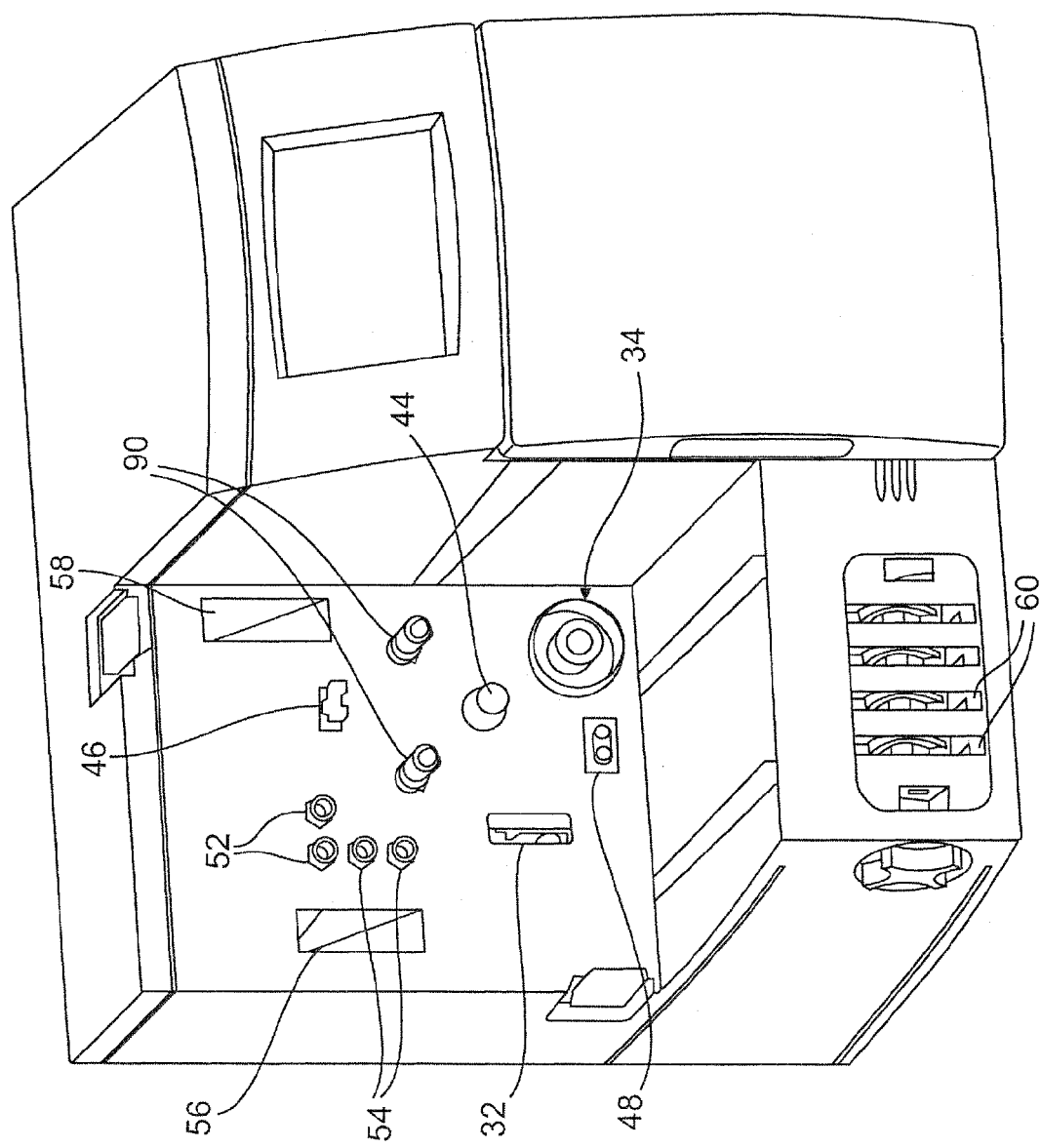
FIG. 3 is a perspective view of the instrumentation device of the present invention.
Figure 4:
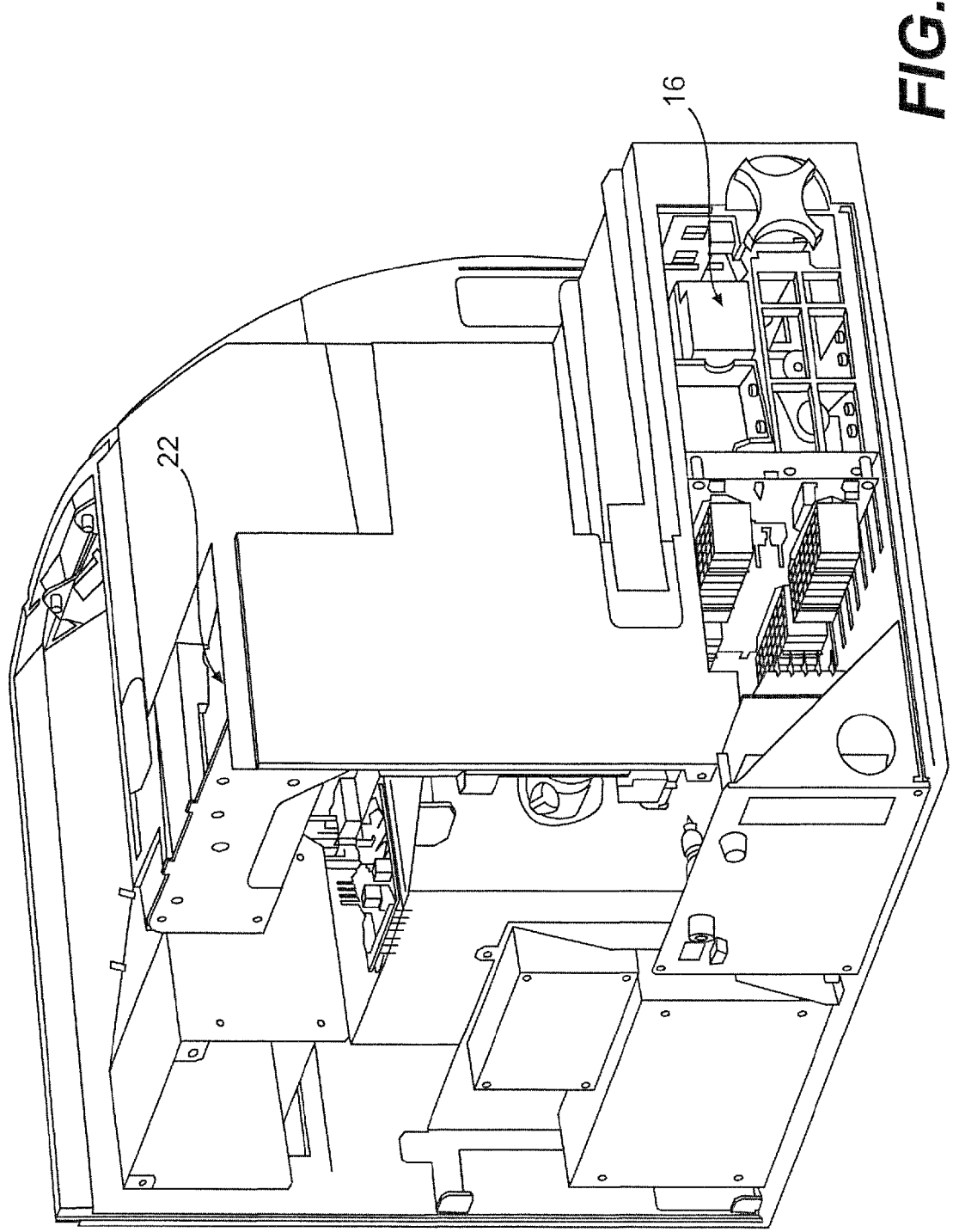
FIG. 4 is a rear and partial side view of the device with covers removed of FIG. 3.

As shown in FIG. 3, the interface features of device 14 include circulation pump drive 34, actuator valves 90 and cycling sensor 32. In addition, a temperature probe 44 and a flow sensor 46 interface with the components of module 12. Device 14 also includes an electrical connection 48 for pH probe 26 disposed within module 12.

Gas ports 52 communicate with gas exchanger 24. One port 52 communicates with the input to exchanger 24 and the other port 52 communicates with the output of the exchanger. Gas ports 54 control pressure to the cycling fixture 40. One port 54 communicates with the IC chamber and the other port 54 communicates with the EC space. As viewed from the front, the left port 52 is the exchanger output and the right port 52 is the exchanger input. The top port 54 is the IC reservoir pressurization port, and the lower port 54 is the EC reservoir pressurization port.

As described above, module 12 is heated to maintain cell fluid temperature. Heating mechanism 22 (FIG. 6) maintains the cell environment to promote growth and production. The cell culture, disposable modules 12 requiring elevated temperatures are warmed by fully encapsulating the module and attaching the module to the controlling instrument 14, such that air ports are aligned and warmed air is forced into the module from the instrument at one location and allowed to escaped at another. Instrument device 14 has a heated air outlet 58 and a return heated air inlet 56.

When disposable module 12 is installed onto the controlling instrument device 14, the air inlet 88 (FIG. 19) of the disposable module aligns with the air outlet 58 of the controlling instrument. Heating mechanism 22 forces warmed air through outlet 58 and into the warmed air inlet 88 and into disposable module 12. The warmed air elevates the temperature of the components inside of the module. The exhaust air exits through air outlet 86 and into air inlet 56 of instrument device 14 where it is circulated through recirculated.

Figure 19:
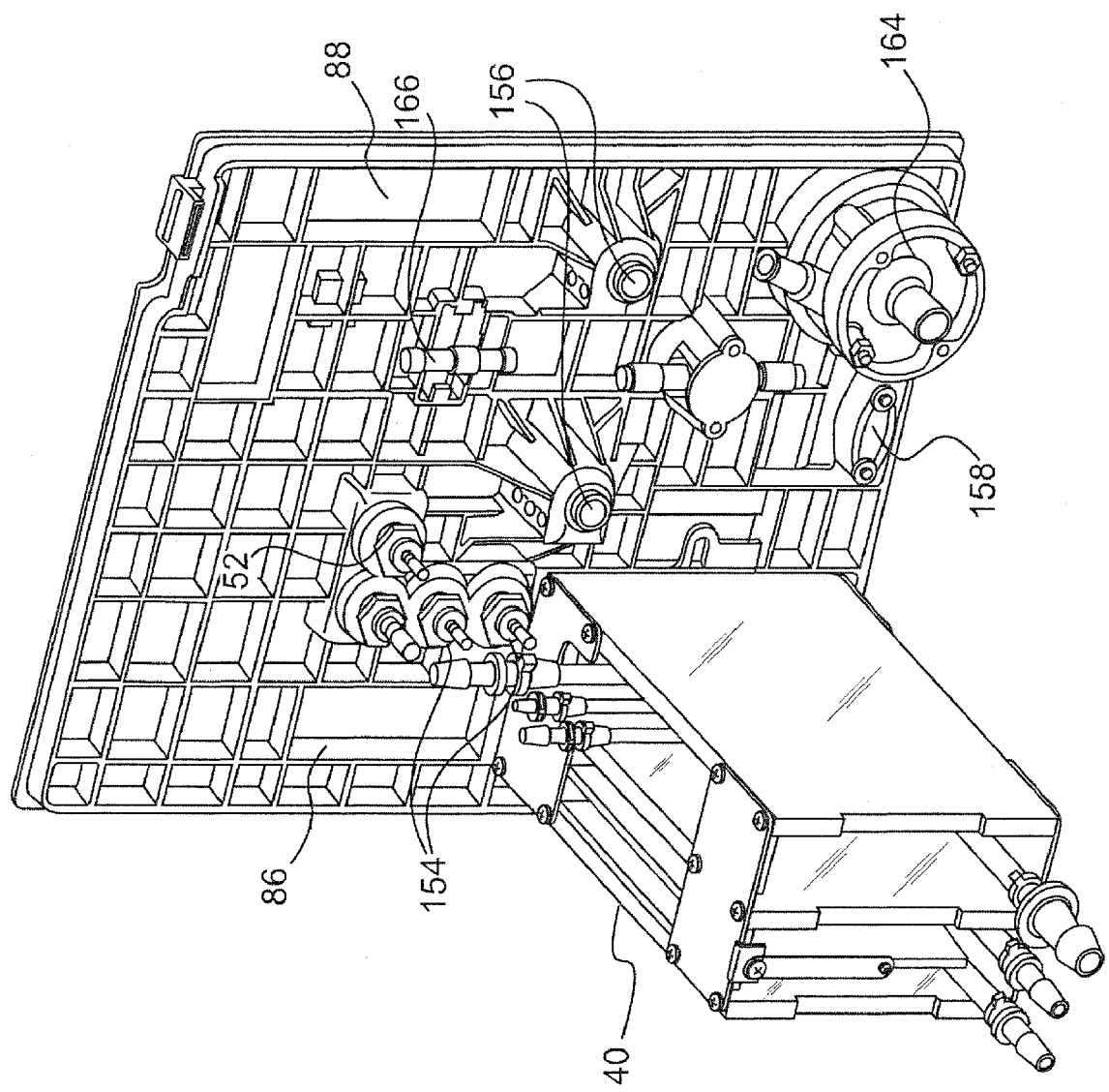
FIG. 19 is a perspective interior view of the back of the module of FIG. 17.

During installation, module 12 is aligned with the connections of the device 14 and the module is placed into the operating position as shown in FIG. 10. All mating interface features are functional. Referring to FIG. 19, when installed, certain features of the module 12, formed in a back panel 148 of the module, interface with device 14. Module air outlet 86 aligns with device air inlet 56 and module air inlet 88 aligns with device air outlet 58 to circulate heated air through module 12 as described herein. Gas connectors 152 and 154 engage device gas ports 52 and 54, respectively, to allow gas to enter and exit module 12. Valve bodies 156 receive actuator valves 90. Hub 158 receives pH probe 26 interface and aligns with electrical connector 48. Module 12 is connected to circulation pump drive 34 via module pump connection 164. Cycling unit 40 also communicates with cycling sensor 32 when the module is installed. The flow sensor 46 of device 12 mates with flow sensor connection 166, The temperature sensor 44 of device 14 mates with a non invasive receptacle in module 12 that is in contact with the IC media to provide control feed back to the control mechanism to regulate the thermal output of heater 22. The above mating connections facilitate the one-motion installation of the module 12 on the device.

Figure 7:
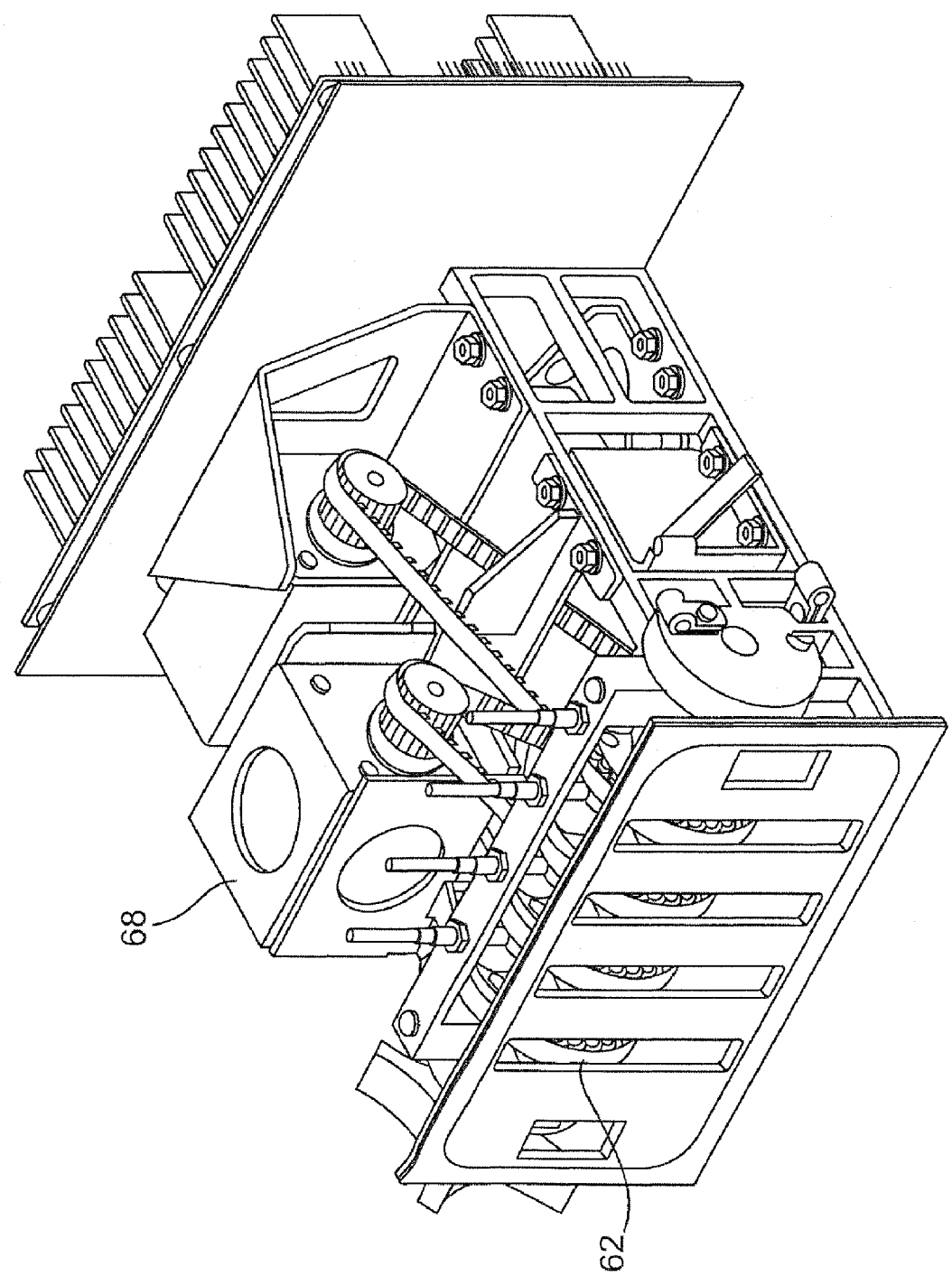
FIG. 7 is a perspective view of the variable output pump of the system of the present invention.
Figure 8:
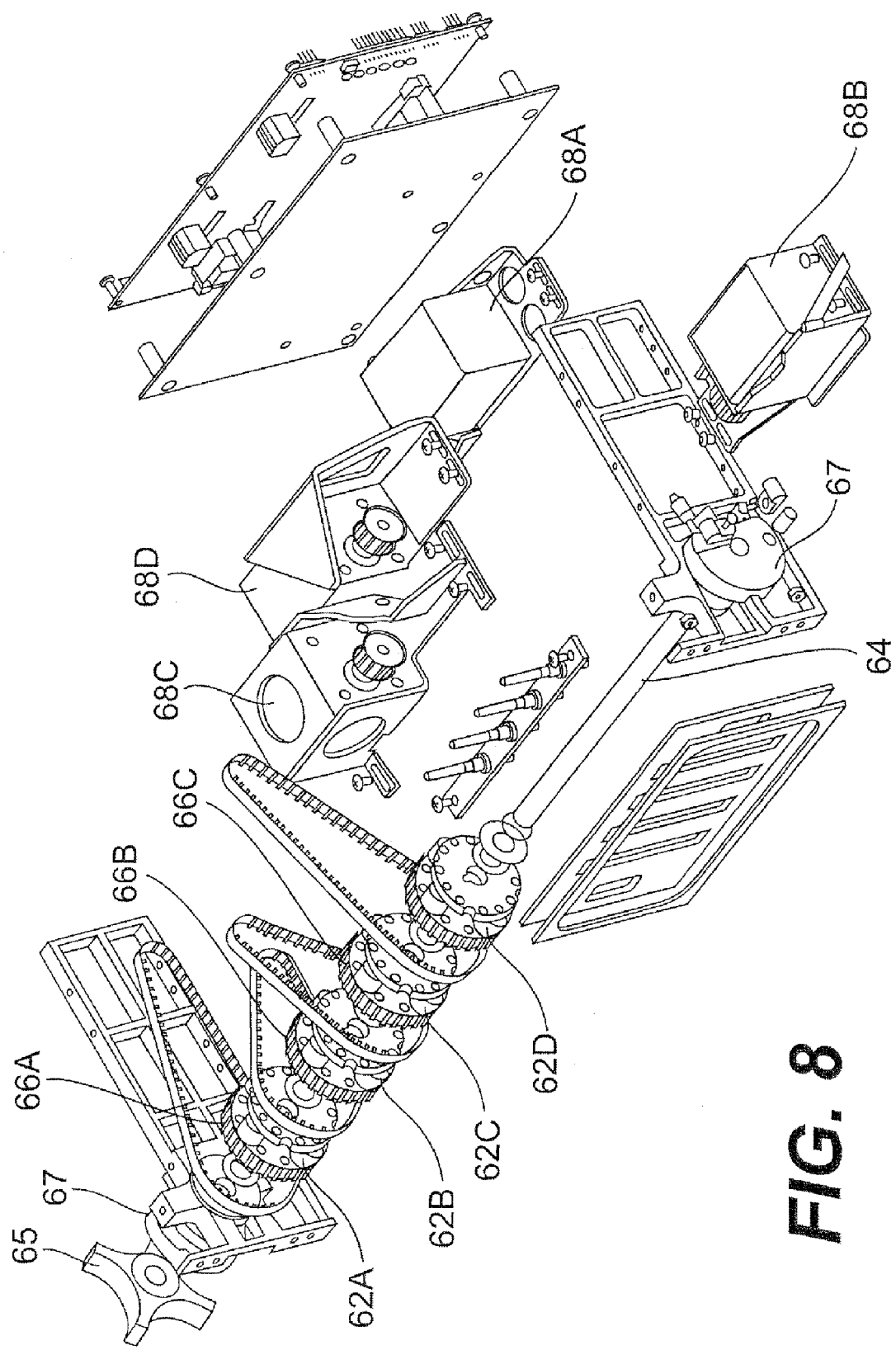
FIG. 8 is an exploded view of the pump of FIG. 7.
Figure 9:
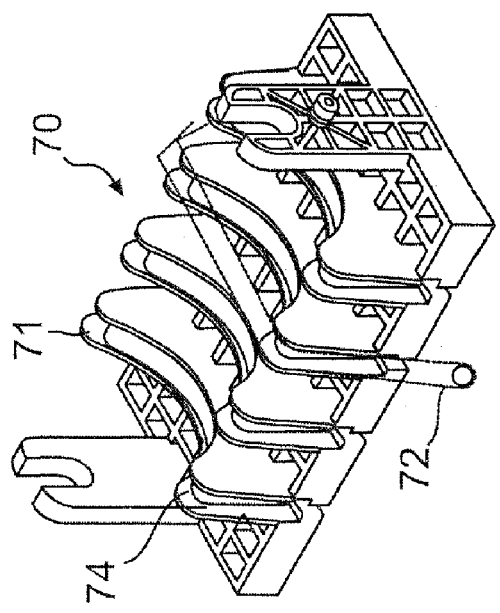
FIG. 9 is a perspective view of the pump cassette of the system of the present invention

Referring to FIGS. 7-9, the present invention incorporates a multi-position, cassette loading, and peristaltic pump 16 (FIG. 2) with discrete, variable output control for each channel. A plurality of channels 60 (FIG. 3) are located in device 14. Although four channels are shown, it should be appreciated that pump 16 could have more or less channels.

As shown in FIG. 8, the pump has individual, variable control of the output of each channel. Pump rotors 62A-62D have a common fixed axial shaft 64 with individual servo drive. The occlusion rotors 66A to 66D are mounted to the pump rotors 62A-62D, which in turn are mounted on the single shaft 64 with internal bearings that allow for independent functional control by a respective reacting servo drive 68A-D. The single shaft minimizes tolerance accumulations typically caused by misalignment of individual rotors and shafts mating with a multi-channel cassette. Feedback sensors are included to verify rotation of the pump rotors.

Typical multi-channel peristaltic pump applications operate using a rotating drive shaft that is common to all rotors. This causes all rotors to turn at the same revolution per minute (RPM), yielding the same fluid output. Different inside diameter tubing may be used to give a fixed ratio delta output from one rotor to another. To obtain a variable output of the peristaltic pump segments, individual pump heads and drives are used. This requires individual tubing cassettes that must be loaded individually and does not allow for close center to center distance between pump heads.

As shown in FIG. 9, a multi-channel cassette 70 is featured with pre-loaded peristaltic tubing 72 to reduce loading errors and to reduce installation time. The mechanism includes a cam operated cassette insertion feature 74) that interfaces with 67 on pump 16. As shown in FIG. 8, a knob 65 is rotated to move earn feature 74 into position to aid initial tubing occlusion during loading.

The cassette configuration is structured to hold multiple peristaltic tubing segments. A gripping feature 76 on the top and the bottom prevents the tubing from creeping during operation. The design allows for all tubing segments to be loaded into the pump drive mechanism at the same time. A latching feature 74 is also included to provide a bearing surface for the cam-operated latch 67 to react upon.

Figure 24:
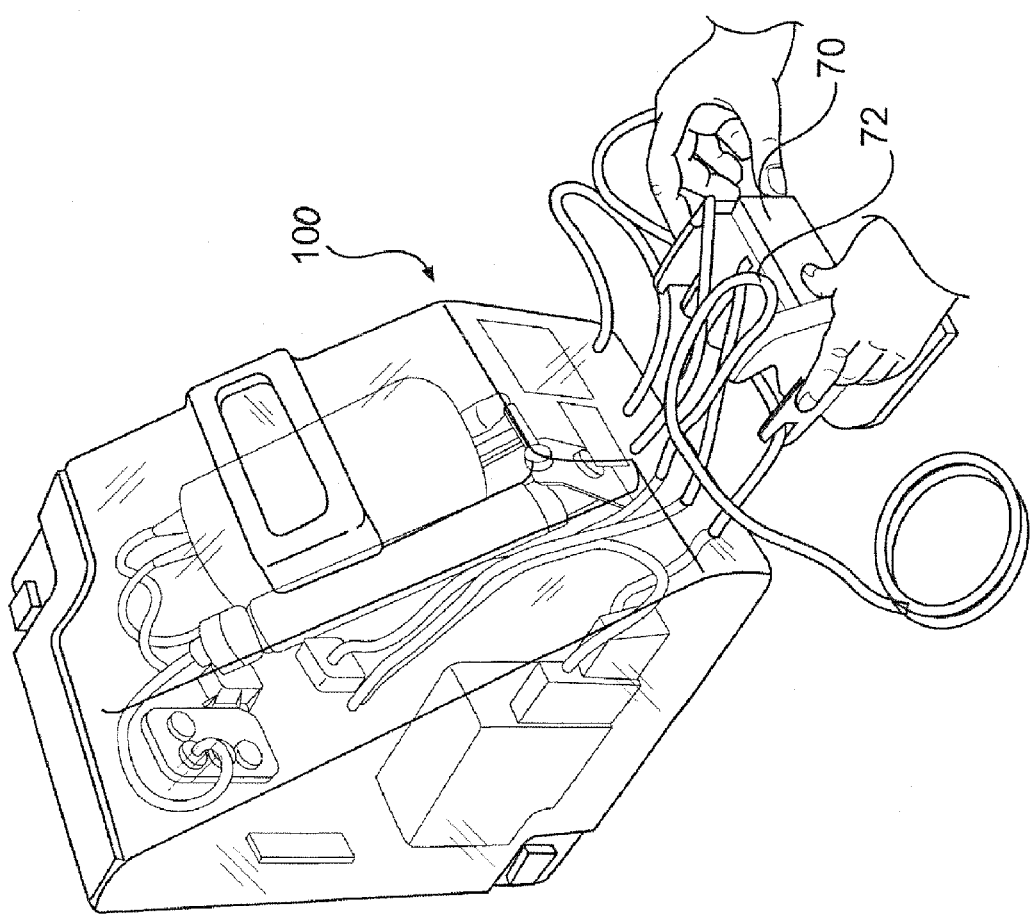
FIG. 24 is another perspective view of the module of the present invention.

Referring back to FIGS. 1 and 2, cassette 70 is pre-loaded with peristaltic tubing (FIG. 24) and positioned in groove 80 on module 12. After module 12 is positioned on device 14, cassette 70 is removed and inserted into interface or plate 82. Each cassette section 71 (FIG. 9) supporting the tubing is inserted into a respective channel 60 (FIG. 3) of the interface 82. This configuration reduces tubing segment loading errors with pre-loaded multi-position cassettes, and reduces installation time.

Figure 12:
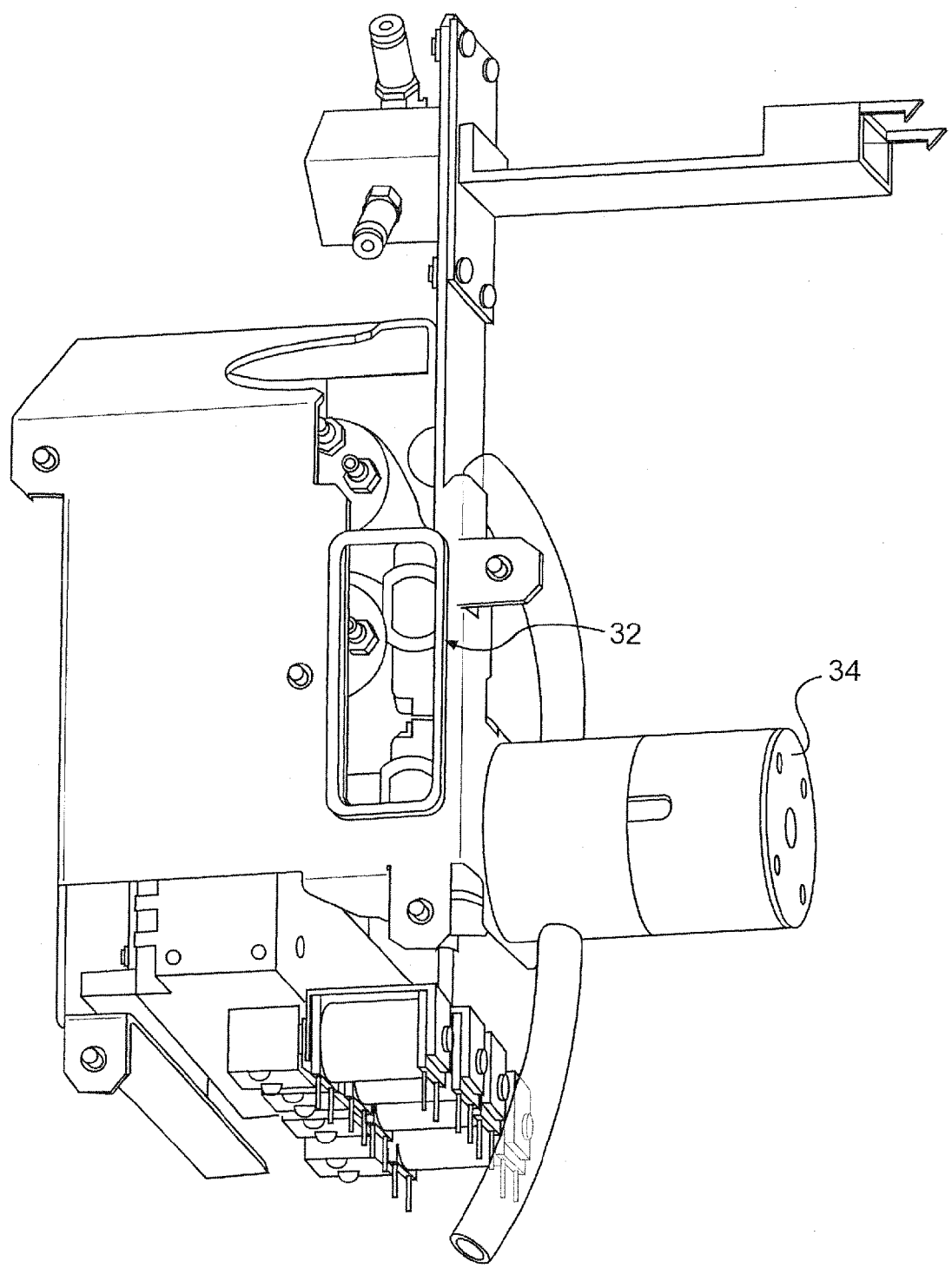
FIG. 12 is a front view of the fluid cycling control of FIG. 11.
Figure 20:
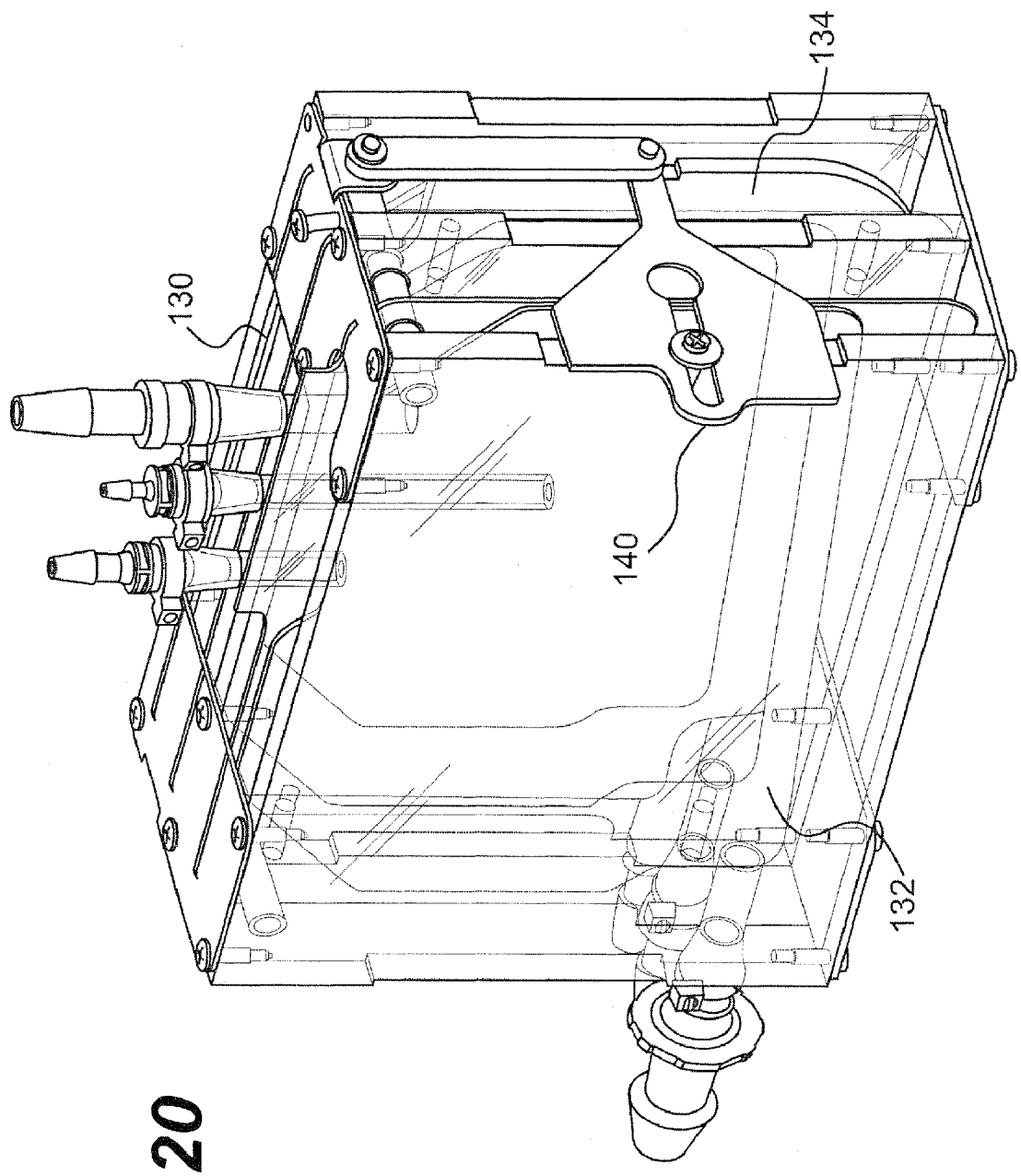
FIG. 20 is a perspective view of the extra-capillary cycling unit of the present invention.
Figure 21A:
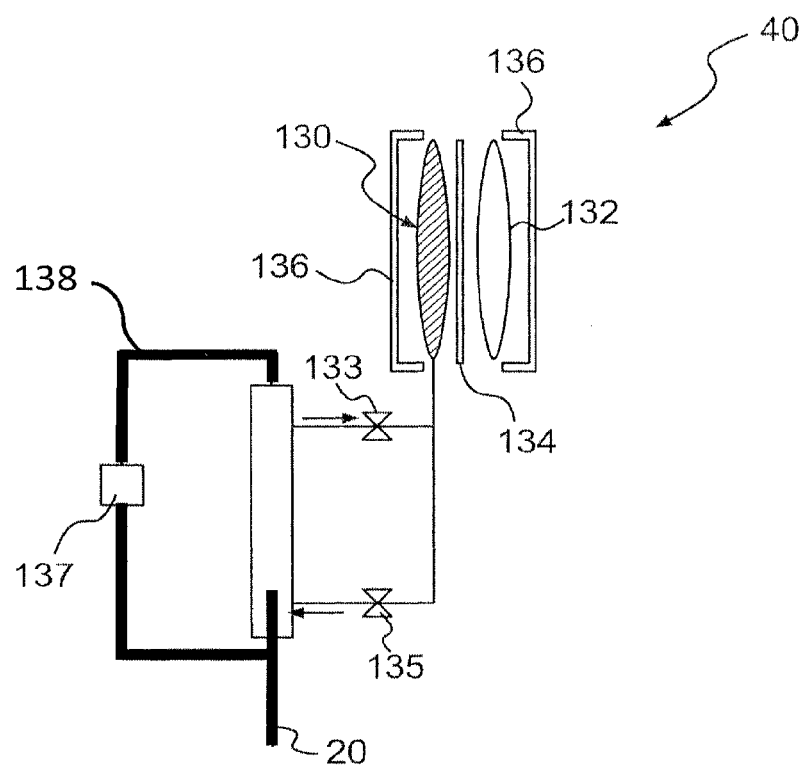
FIG. 21A is a flow diagram of the cycling unit of FIG. 20.
Figure 21B:
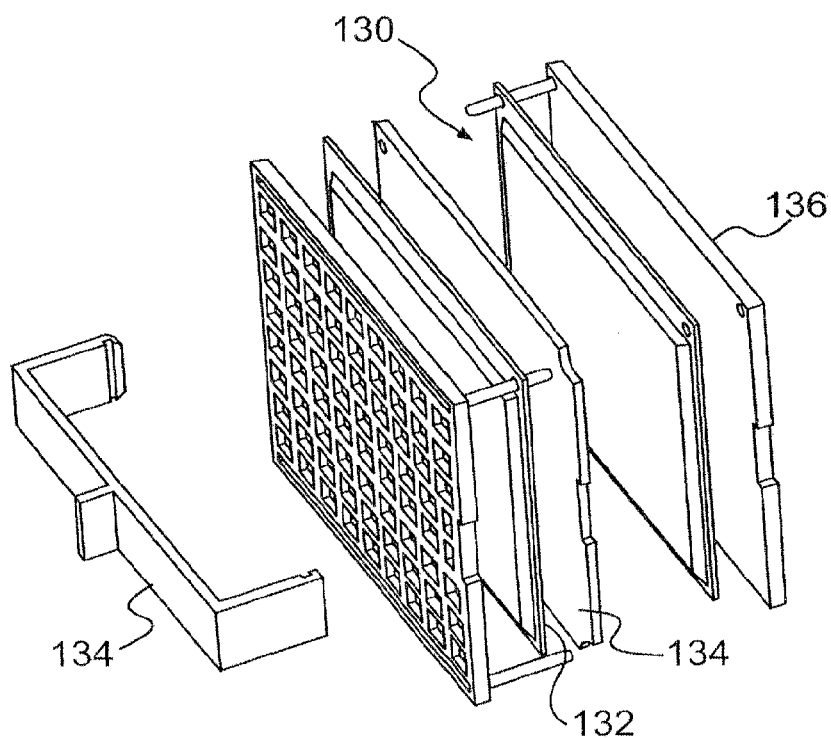
FIG. 21B is an exploded view of the cycling unit.

Referring to FIGS. 11 and 12, valves and sensors 32 in the instrument control the fluid cycling in the cultureware module 12. Two optical sensors detect the low or high position of the cycling position sensor flag 140 (FIG. 20). This information is used by a predictive algorithm to control the pressures applied to the IC chamber and EC pressure bag to effect cycling.

Figure 14A:
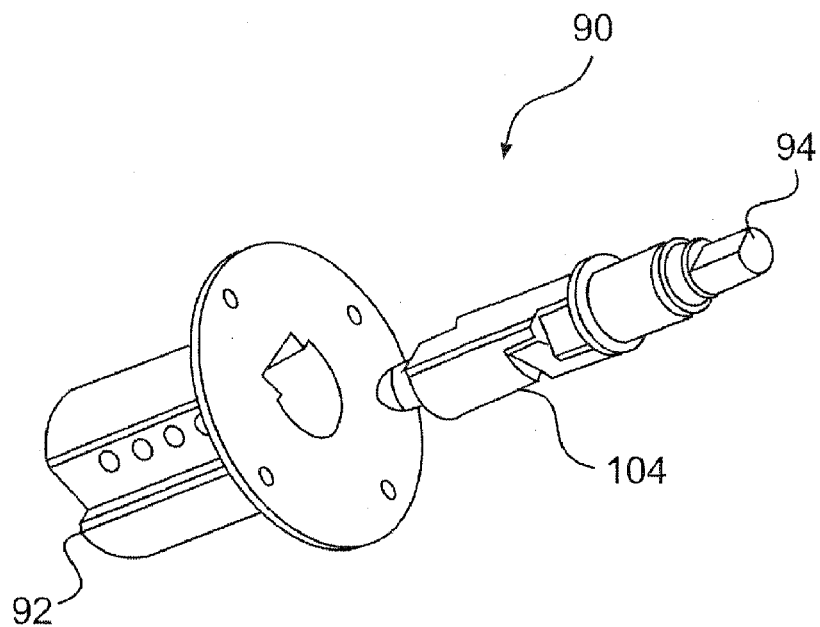
FIGS. 14A and 14B are exploded views of the valve rotor of FIG. 13. and the body used with it.
Figure 14B:
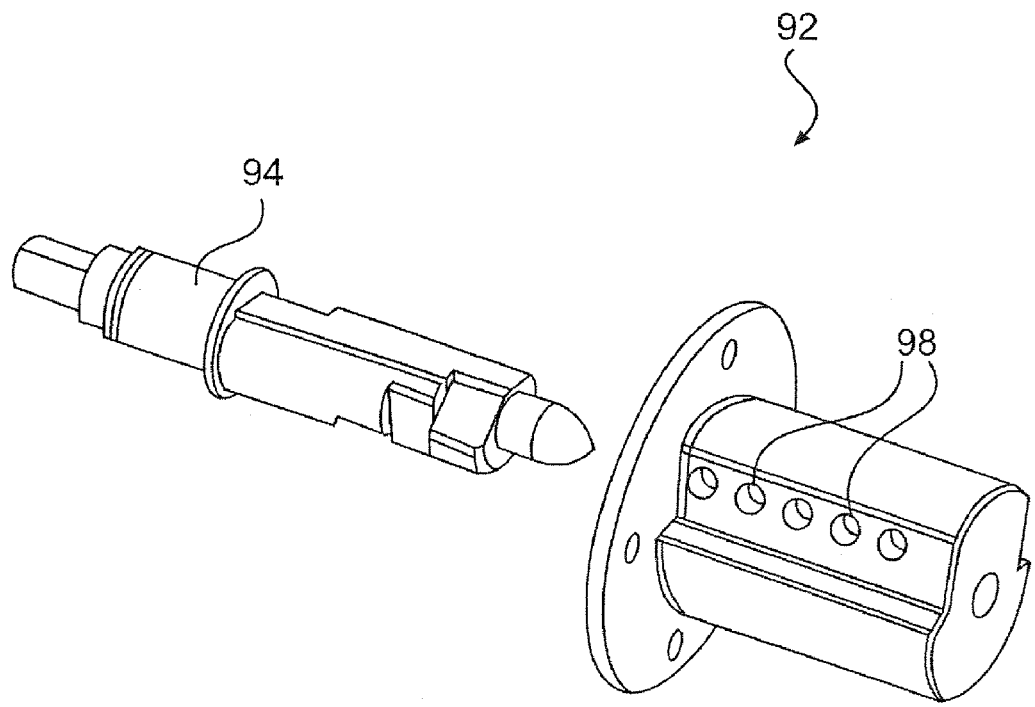
Figure 14C:
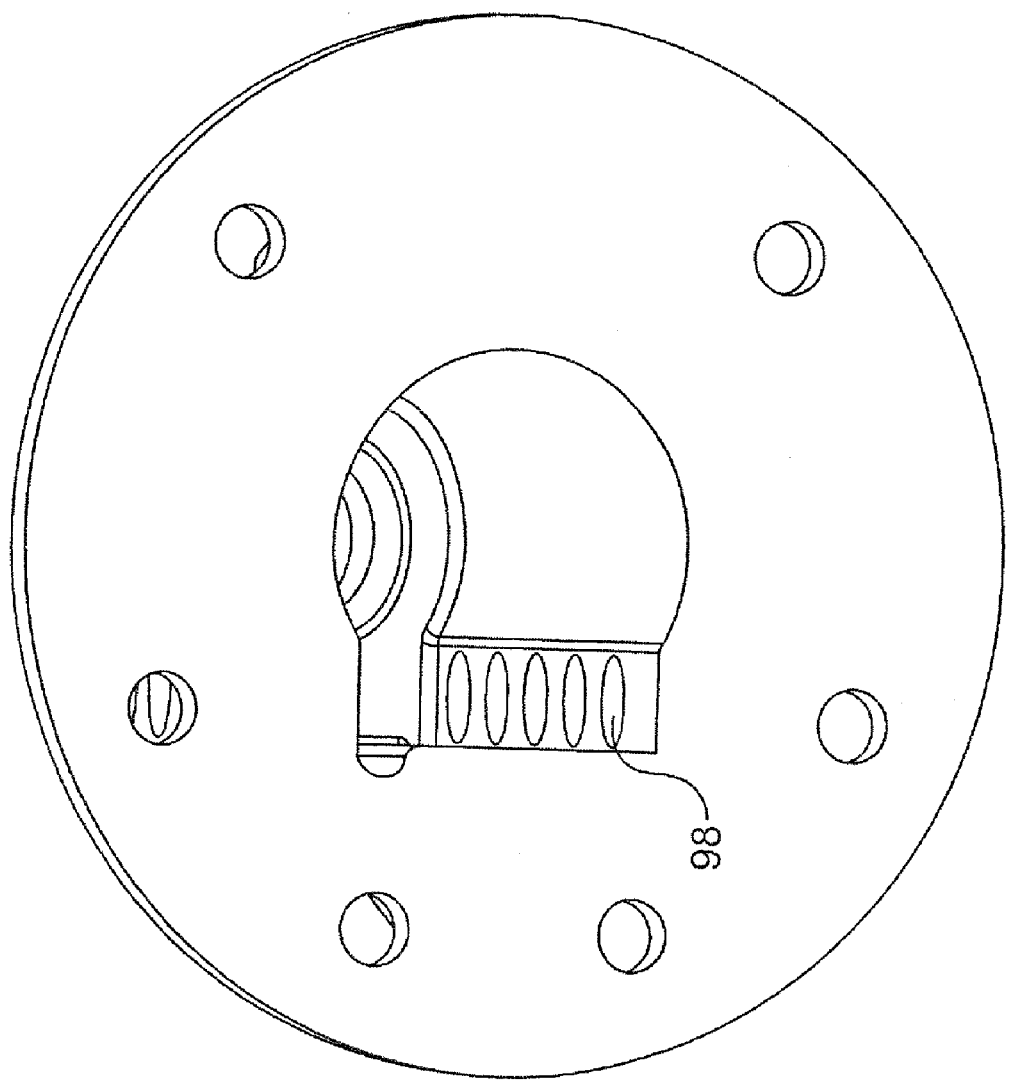
FIG. 14C is a rear view of the valve body.

Sterilizable, disposable, actuator driven, rotary selection valves 90 are shown in detail in FIGS. 13-14C. Valve 90 comprises a valve housing 93 and valve cam 94. The elastomer tubing (not shown) is insertable through openings 98 in valve body 92 and is occluded by a rotating cam 94 that compresses the tubing against the valve body. This is accomplished by using a controlled, incremental, servo drive 96 (actuator and position feed back loop) to move cylindrical cam that reacts against immobile valve body 92 that holds the tubing in a constrained state. The cam design allows for a high area of the cam 104 to occlude the tubing and a low area of the cam 106 not to occlude, resulting in a closed and open condition respectively. Cam rotational positioning features may also be added to move cam 94 to predetermined positions. Configurations can be structured to accommodate multiple tubing segments in one device. The two piece design allows for fluid contact portion of the valve to be molded into the backpanel 148 (FIG. 19) as a hub 156 and to be sterilized (EtO, chemical or radiation) with the rest of the fluid circuit and eliminates the need to be added separately.

The design of this clamp is meant to be used in an automated cell culture application where a disposable cultureware module interfaces with an electro-mechanical instrument. The combined unit is to be automated, which required various tubing lines of the disposable to be occluded/open to provide automated process control. The selector valve is used to automatically open and close tubing lines to direct fluid or gas flow during process control. Minimizing operator set-up is also a requirement. The disposable cultureware must be inserted into the instrument in an operating position with no special operator procedures required for loading the tubing into the clamps. Existing technologies did not meet these requirements, because the manual clamps were not automated, and solenoid valves required a special operator loading procedure.

In the cell culture system of the present invention, the fluid path must be free of unwanted organisms (sterilized). Commercially available selector valves are not gas sterilizable. Sealing surfaces of the selected position may be unexposed to the gas sterilant and those surfaces may be "non-sterile" when the valve is repositioned. Valve 90 provides automated actuation of the cam, compactness, multiple lines, maintains valve position even with loss of actuator power, the disposable valve body is less costly than an equivalent switching valve, and can be incorporated into the back panel of 12. Offset occluded/open cam positioning of two tubing lines can insure a make-before-break switching of fluids. No power is required to maintain any operating position, and tubing segments used in the valve body can be sterilized.

It should be appreciated that a solenoid driven pinch mechanism, can be used in place of the actuator valve. This application may utilize a piston plunger actuated by an electrical coil to provide linear motion to pinch the tubing. A manual pinch clamp could also be used. The clamping position is manually activated by a mechanical bearing surface compressing the tubing and then held in position by a detent feature. This clamp type requires manual deactivation. A membrane over the series of ports could also be used. The membrane is actuated against the port to seal it. Multiple ports are configured for use as a selector mechanism.

Figure 15B:
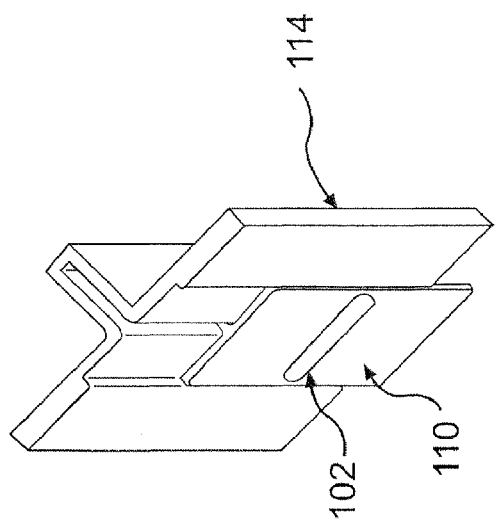
FIGS. 15A-15C are perspective views of a tubing slide clamp of the present invention
Figure 15C:
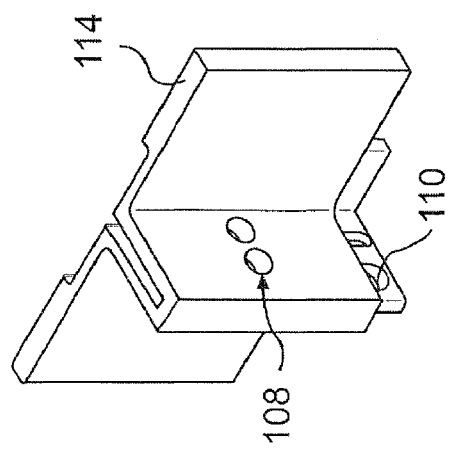
Figure 15A:
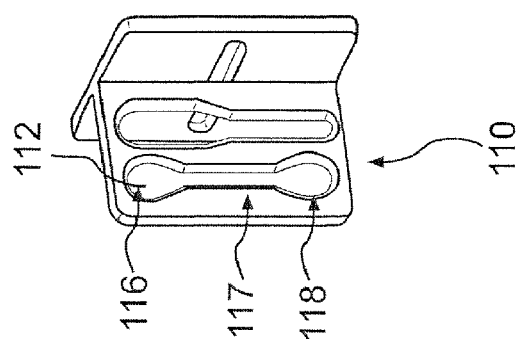

In another embodiment shown in FIGS. 15A-15C, an actuator driven tubing slide clamp 110 with multiple positions and multiple tubing can be used as an alternative to valves 90. Elastomer tubing is occluded by sliding the tubing into a narrow slot 112 that compresses the tubing wall against itself. This is accomplished by using a servo drive (actuator and position feed back loop) to move a plate 110 with slot 112 in it and reacting against another plate or slide body 114 that holds the tubing in an immobile state. The moveable plate is designed with varying width slots to allow for position/positions to be inactive. This allows for normally open 116 or 118 and normally closed 117 positions. Configurations can be structured to accommodate multiple tubing segments in one clamp.

In operation, slide 110 is positioned into slide body 114. Tubing is inserted through tubing ports 108 and slide 110 at position 116 where both tubes are not occluded. A remote servo (not shown) engages into server drive slot 102 and moves the slide to position 117 where one tube is occluded and one tube is not occluded. The remote Servo than moves the slide to position 118 where the occluded tube from the previous step is not occluded, and the tube from the not occluded tube from the previous step is now occluded. When moving the slide from position 117 to position 118, both tubes are occluded to insure that one tube is occluded before the other tube is opened. It should be appreciated that the number of tubes and configuration of the slide can be modified to meet customized applications.

The clamp is meant to be used in an automated cell culture application where a disposable cultureware module interfaces with an electro-mechanical instrument. The combined unit is to be automated, which required various tubing lines of the disposable to be occluded/open to provide automated process control. During process control the clamps are open/closed to simulate the function of an expensive, "disposable" switching valve. Minimizing operator set-up is also a requirement. The disposable cultureware must be inserted into the instrument in an operating position with no special operator procedures required for loading the tubing into the clamps. It provides automated actuation of slide clamp, compactness, multiple lines, maintains clamp position even with loss of actuator power, less costly than an equivalent switching valve. Offset occluded/open position of two tubing lines can insure a make-before-break switching of fluids. No power required to maintain any operating position.

Figure 16:
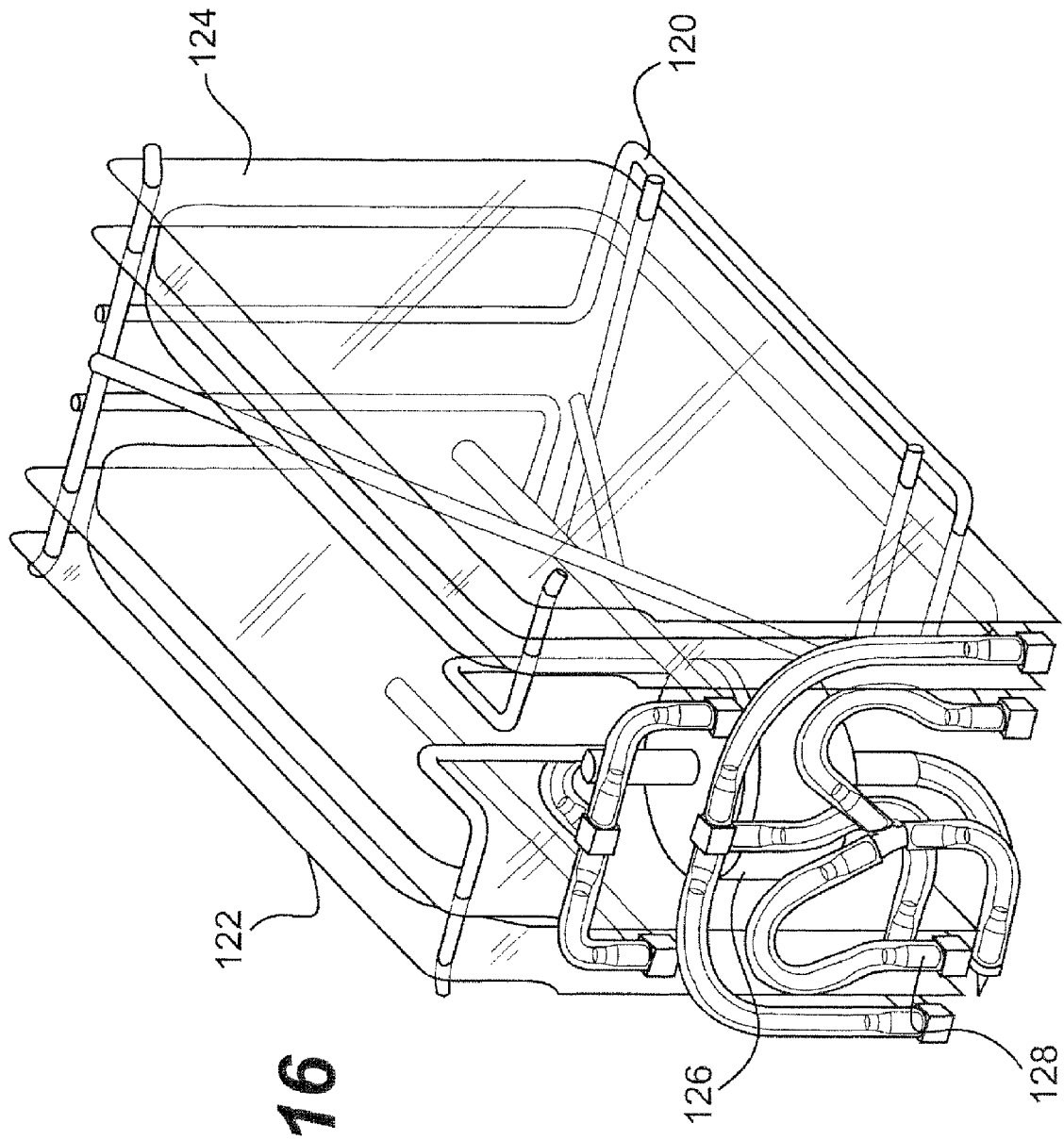
FIG. 16 is a perspective view of the factor and harvest bags of the present invention.

As described above, integrated cool storage area 18 maintains growth factors and harvested cells or cell products at a low temperature (approximately 4° C.). Referring to FIGS. 2 and 16, a rack 120 is removably positionable within cool storage area 18. Rack 120 is designed to support a plurality of bags 122, 124. The bags are used to contain the smaller quantities of product or growth factors. It should be appreciated that other solutions can be disposed with the bags. For example, high molecular weight growth factor can be located with bag 122. This factor is connected via tubing 128 to the bioreactor or cell growth chamber 20 and the flow controlled by pump 16. Harvested cells or cell products can be stored in bag 124. A cell filter 126 is provided to provide additional filtration. A filter bypass line is included if filtering of the harvest is not desired as in the case of cell collection. After the process is complete the cells can be removed from the cell culture chamber via the tubing and stored in bag 124 until use.

Figure 17:
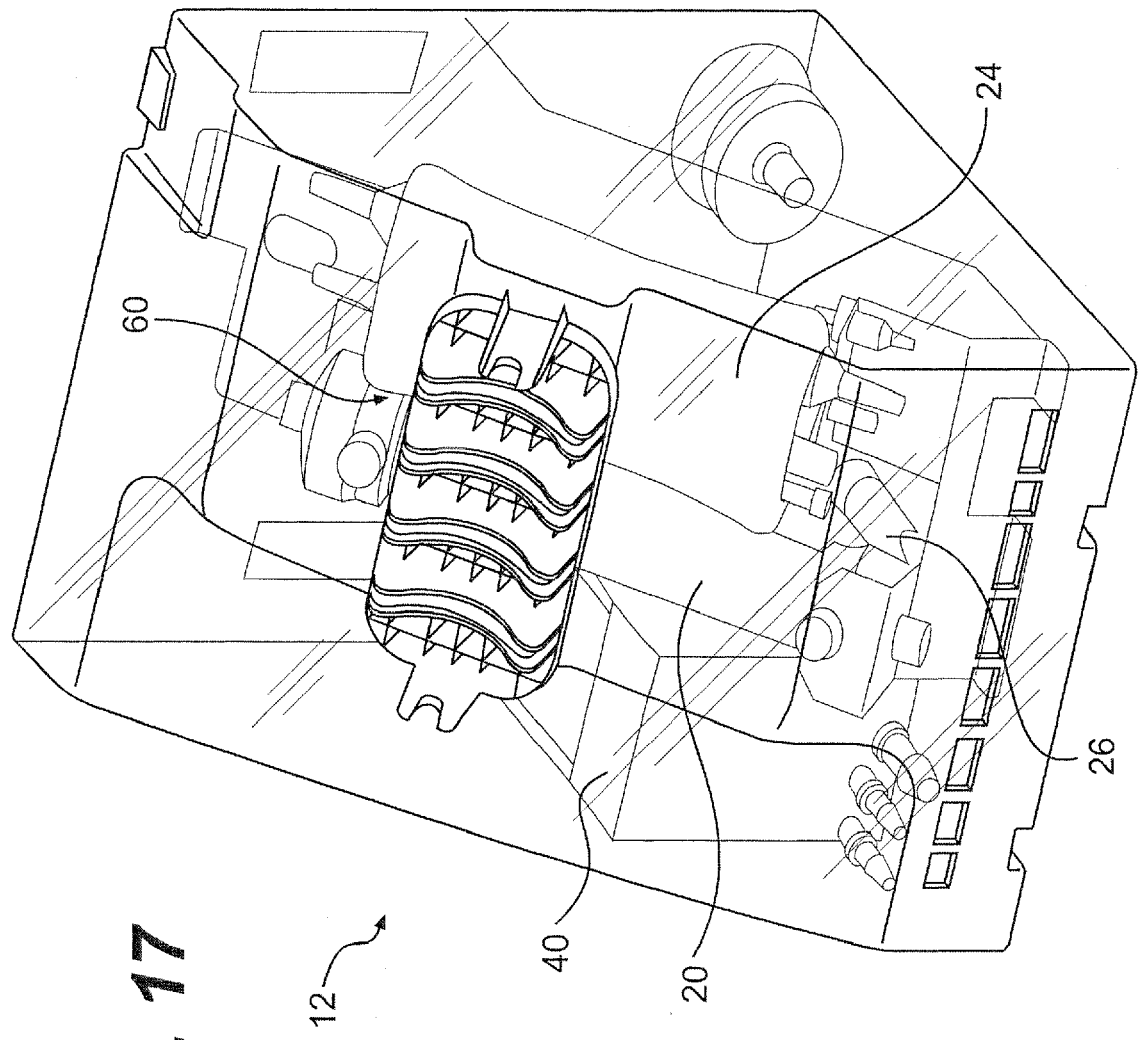
FIG. 17 is a perspective view of the disposable culture medium module of the present invention.
Figure 18:
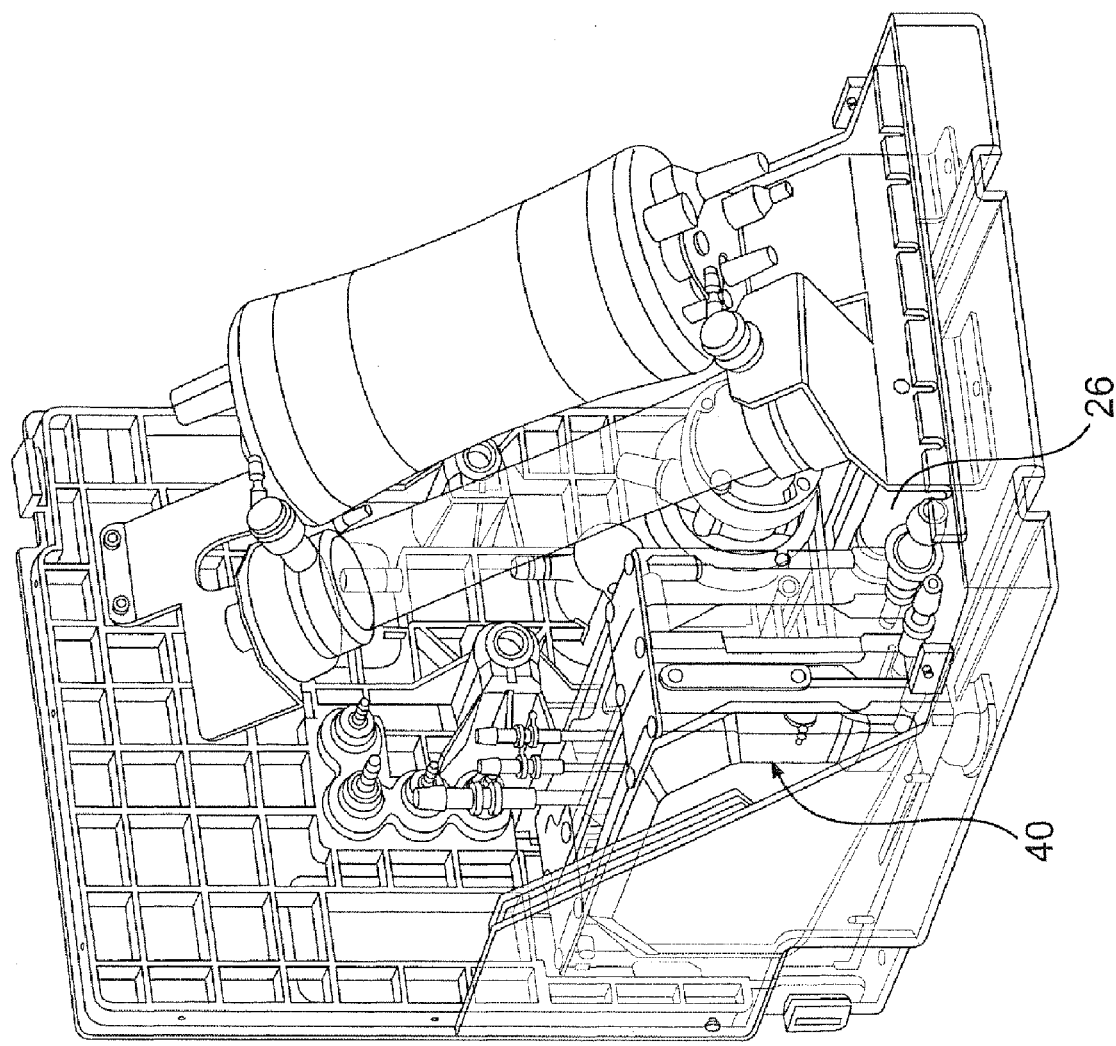
FIG. 18 is an interior view of the module of FIG. 17.

As shown in FIGS. 17-19, disposable cultureware module 12 includes fluid cycling unit 40 to maintain fluid volumes and cycling in the cell growth chamber. Referring to FIGS. 18-21, the present invention utilizes extra-capillary (EC) cycling in cell culture growth chamber 20 (FIG. 17) utilizing a non-rigid, EC reservoir 130 and mechanical or a second flexible reservoir 132 to cause elevated EC pressure. Reservoirs 130, 132 are separated by a sensor plate 134. Reservoirs 130, 132 are restricted in the maximum amount of expansion by a rigid mechanical housing 136. EC cycling is achieved by utilizing a non-rigid reservoir to retain the varying fluid volume associated with an EC circuit. Flexible reservoir 130 is fluidly connected to the bioreactor or hollow fiber device 20. Second flexible reservoir 132 is pressurized to apply force against the flexible reservoir 130 to provide an elevated EC pressure to cause an ultra-filtrative condition and force fluid into an intra-capillary (IC) circuit 138. A mechanical feed back position indicator 140 is physically connected to sensor plate 134 and moves with the physical expansion and contraction of the first flexible reservoir. The position of indicator 140 is sensed by the position sensors 32 and is used to control the force that is applied by second flexible reservoir 132. It should be appreciated that an alternate mechanical force apparatus may be used instead of a second flexible reservoir to cause pressure changes.

During operation the pressure is increased in the IC circuit 138 by pressurizing an IC reservoir 137. This pressure causes an ultra-filtrative condition that forces fluid transmembrane across the semi-permeable matrix of the bioreactor 20. The fluid is then forced through the connect tubing, through a flow control valve 133 and into the EC reservoir 130. Externally controlled pressure in the pressure reservoir 132 is allowed to vent. The expanding EC reservoir 130 forces the sensor plate 134 toward the pressure reservoir 132 and compresses it. Sensor plate 134 moves external position flag 140 and this is sensed when EC reservoir 130 has filled enough to expand to the EC upper level. The external position sensor 32 senses this position and the pressure in the IC reservoir 137, is decreased and the pressure in the pressure reservoir 132 is increased. This causes an ultra-filtrative condition and forces fluid out of the EC reservoir through a control valve 135, transmembrane across the matrix of the bioreactor 20 and into the IC circuit 138. The sensor plate 134 moves the external position flag 140 and the sensor 32 senses when the EC reservoir 130 has contracted to the EC low level.

The EC cycling unit of the present invention offers fluid dynamics to cause fluid flow in the EC space thus minimizing nutrient and metabolic waste gradients that may be detrimental to the cells. It provides fluid level control without the use of ultrasonics or load cells that is not affected by cell debris. The flexible reservoirs are considerably less expensive and are suited for disposable applications. The sealed EC reservoir with cycling also limits contamination and isolates the cells.

The present invention also includes an indirect lactate control method for perfusion culture using $CO_2$ and pH sensing. The method predicts open system, perfusion culture, lactate levels in the circulatory medium by monitoring the pH and off-gas $CO_2$ level. This is accomplished by calculating the initial bicarbonate level of the media then utilizing the liquid pH and gas level of $CO_2$ to calculate current lactate concentration. This is used to control media dilution rate of the cell culture. The resulting calculated lactate value is used to set the perfusion rate of media dilution to maintain a pre-determined lactate level. Thus, an invasive sensing system or multiple off-line sampling is not required.

A physical relationship exists between bicarbonate buffer, dCO2, and pH.

$$pH = pK + \log([HCO_3^-]/dCO_2]) \quad \text{Equation (1)}$$

where:
pH=the pH of the solution
pK=the acid ionization constant for bicarbonate
$HCO_3^-$=the current bicarbonate concentration (mM)
$dCO_2$=the concentration of dissolved $CO_2$ Lactic acid production by the cells appears to be the dominant driving force for pH changes in cell culture media. Based on this observation, each mole of lactic acid produced results in consumption of one mole of bicarbonate as described by the following equation:

$$[HCO_3^-] = [HCO_3^-]_0 - [\text{Lactate}] \quad \text{Equation (2)}$$

where:
$[HCO_3^-]_0$=the initial bicarbonate concentration in the medium (mM)
Lactate=the lactate concentration (mM)

Equation (3) provides a simple relationship—Henry's Law, that equilibrium $dCO_2$ is proportional to the gas phase concentration of CO2.

$$dCO_2 = a(\% CO_2) \quad \text{Equation (3)}$$

where:
a=$CO_2$ solubility conversion (mM/%)
% $CO_2$=concentration of $CO_2$) in the gas phase that is in equilibrium with $dCO_2$(%).

Equation (4) is derived by substituting Equation 2 in Equation 1 as follows:

$$pH = pK + \log\{([HCO_3^-]_0 - [\text{Lactate}])/[dCO_2]\} \quad \text{Equation (4)}$$

Equation 5 is derived by combining Equations 3 and 4:

$$pH = pK + \log\{([HCO_3^-]_0 - [\text{Lactate}])/[a(\% CO_2)]\} \quad \text{Equation (5)}$$

The operating equation, Equation (6) is derived by solving for Lactate in Equation (5):

$$\text{Lactate} = [HCO_3^-]_0 - (a)*(\% CO_2)*10^{(pH-pK)} \quad \text{Equation (6)}$$

The values of pK and (a) were found to be 6.38 and 0.39, respectively.

Upon taking a lactate and pH reading, the value of (a) is calculated. The initial bicarbonate concentration is calculated as the calibration constant. The advantage is that the bicarbonate concentration does not have to be known when using the present calibration method.

Figure 22:
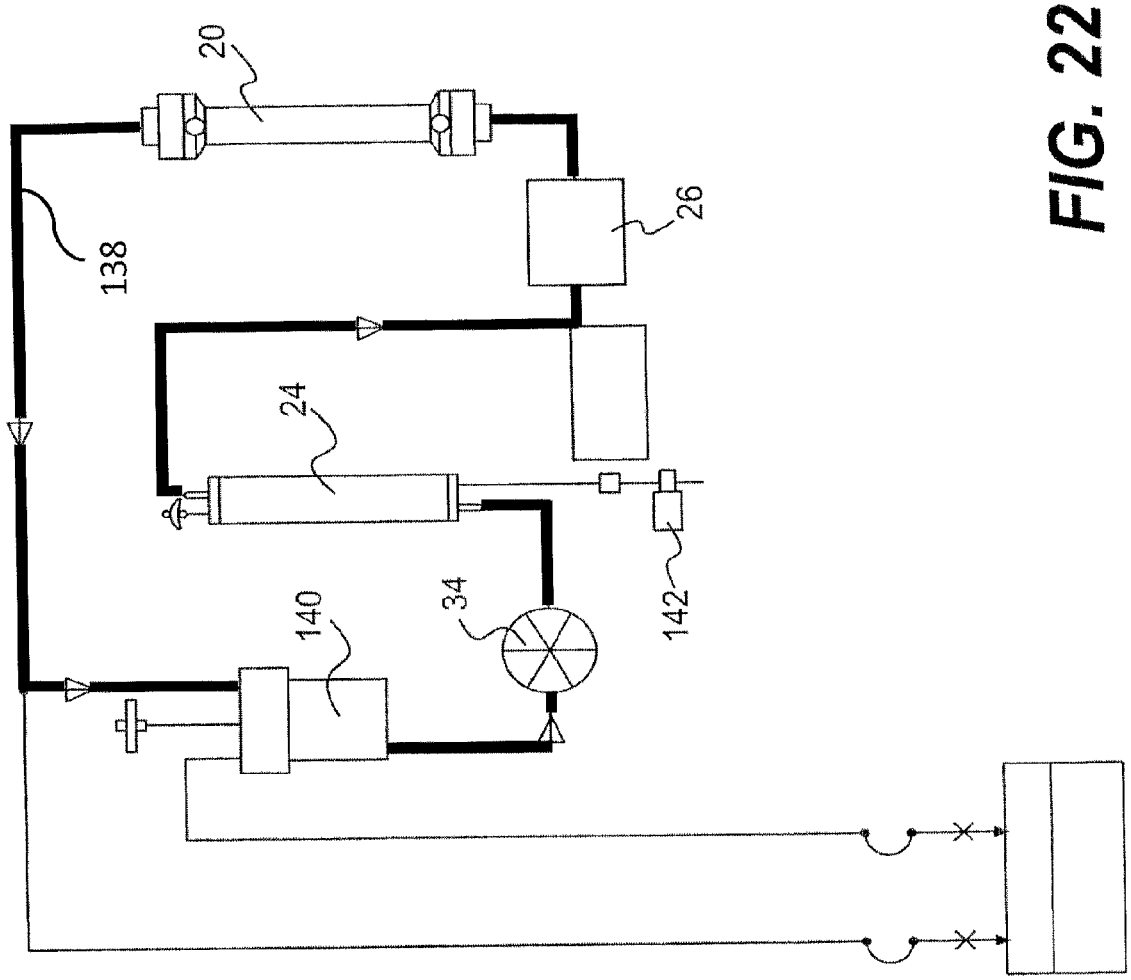
FIG. 22 is a flow diagram of the lactate control system of the present invention.

The application is shown in FIG. 22. In a bioreactor perfusion loop, the growth media is pumped from an IC reservoir 137 via pump drive 34, 164, circulated to the gas exchange cartridge (GEX) 24, pH sensor 26, bioreactor 20, and then back to reservoir 137. Blended gases are passed through the membrane gas exchange cartridge that oxygenates the media and regulates $CO_2$. Per Henry's Law, the $CO_2$ levels in the gas phase or air side of the GEX 24 is in equilibrium with the liquid phase of the media. The discharge end of the GEX is monitored with a $CO_2$ sensor 142 that resides in the device 14 and the lactate is calculated per Equation (6). When the media lactate level is known, the instrument uses automatic, media dilution, control to maintain the predetermined set point.

The present invention utilizes existing signals and with the addition of a non-invasive gas $CO_2$ sensor incorporates lactate control to control media feed rate for cell growth and production. Utilizing the invention reduces materials and labor associated with recurring off-line testing. Utilizing the invention allows for continual adjustment of the dilution rate that would otherwise be inefficient and costly if step increases were used as in previous technologies.

Utilizing the present invention increases the predictability of cell culture metabolics. Allows a perfusion cell culture system to have an increased level of automation. The lactate and media dilution rate can be used to determine the state of cell growth and production.

The present invention also utilizes a novel approach for pH sensing in a cell culture system. Referring back to FIGS. 2, 18 and 19, pH probe 26 and a holder are built into cell culture disposable 12, thus the user is not required to add the probe to the cultureware. Probe 26 is intended to be a one-time use device that is disposed of with the cultureware. The probe is disposed of with the used cultureware, no time is spent recovering the probe for cleaning, revalidating and reuse.

In operation the probe 26, for example, a solid gel filled electrode, is mounted in a holder 28 (FIG. 23) through which the media to be sensed flow. The electrode in the holder is fluidically connected to the cultureware circuit, mounted in the cultureware module, the circuit is checked for fluidic integrity, and sterilized with the completed cultureware (ethylene oxide, EtO). After sterilization, QC checks are performed on the EtO process to provide high confidence of sterilization. When an operator wishes to culture cells, the cultureware is removed from the pouch, loaded on the instrument and fluid is introduced into the cultureware. A period of time is given to re-hydrate the electrode. The cultureware is brought to operating conditions, the electrode is calibrated and then used to control pH in the cultureware. When the cell culture is complete, the operator disposes of the cultureware and the probe. Although the probe has been described as a solid gel electrode other probe types could be used (e.g. an ISFET, liquid filled, immobilized phenol matrix, fluorescence, etc).

Figure 23:
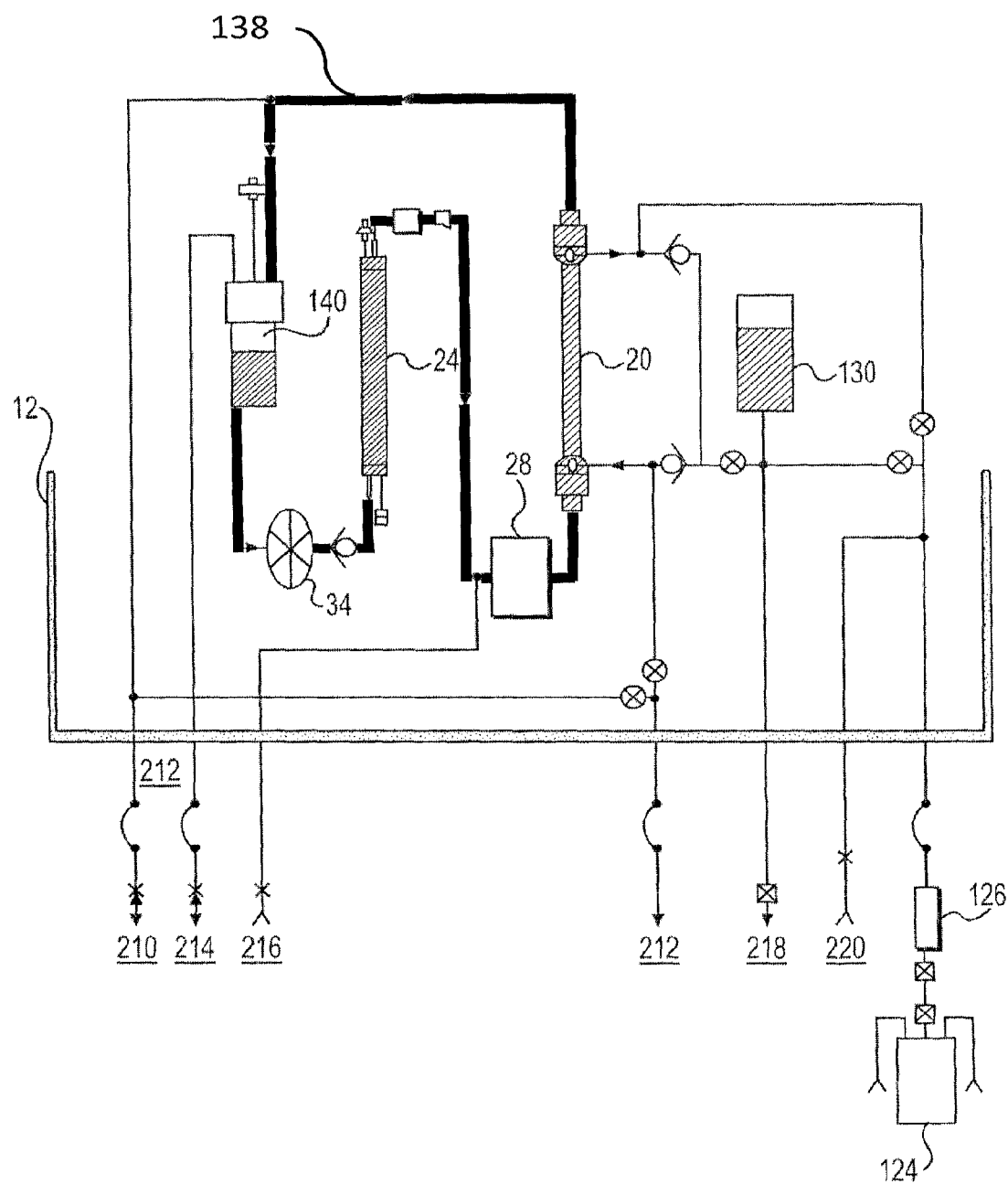
FIG. 23 is a flow diagram of the system of the present invention.

Referring to the flow diagram of FIG. 23, pump 16 moves fresh basal media into the cultureware at media line 210. Media line 210 is connected to a user provided container of fresh media to provide the growth nutrients to the cell culture that are pumped into the disposable. Outflow line 214 is connected to a user provided container to collect the waste or spent media being pumped out of the disposable. Factor line 212 is connected to a user provided container of growth factors that are pumped into the disposable. EC inoculate can be added at 220 and IC sample at 216. Product harvest is removed at 126. The cells are harvested at 218. Harvest line 218 is a pre-attached container that is part of the disposable that is used to collect the product that is pumped out of the disposable. Pump 16 has multiple lines 210, 214, 212 and 126. Because the pump of the present invention has a common fixed axial shaft and individual servo driven rotors, the control of the flow of each can be independent, allowing one channel or flow to be increased while another decreased.

Figure 25:
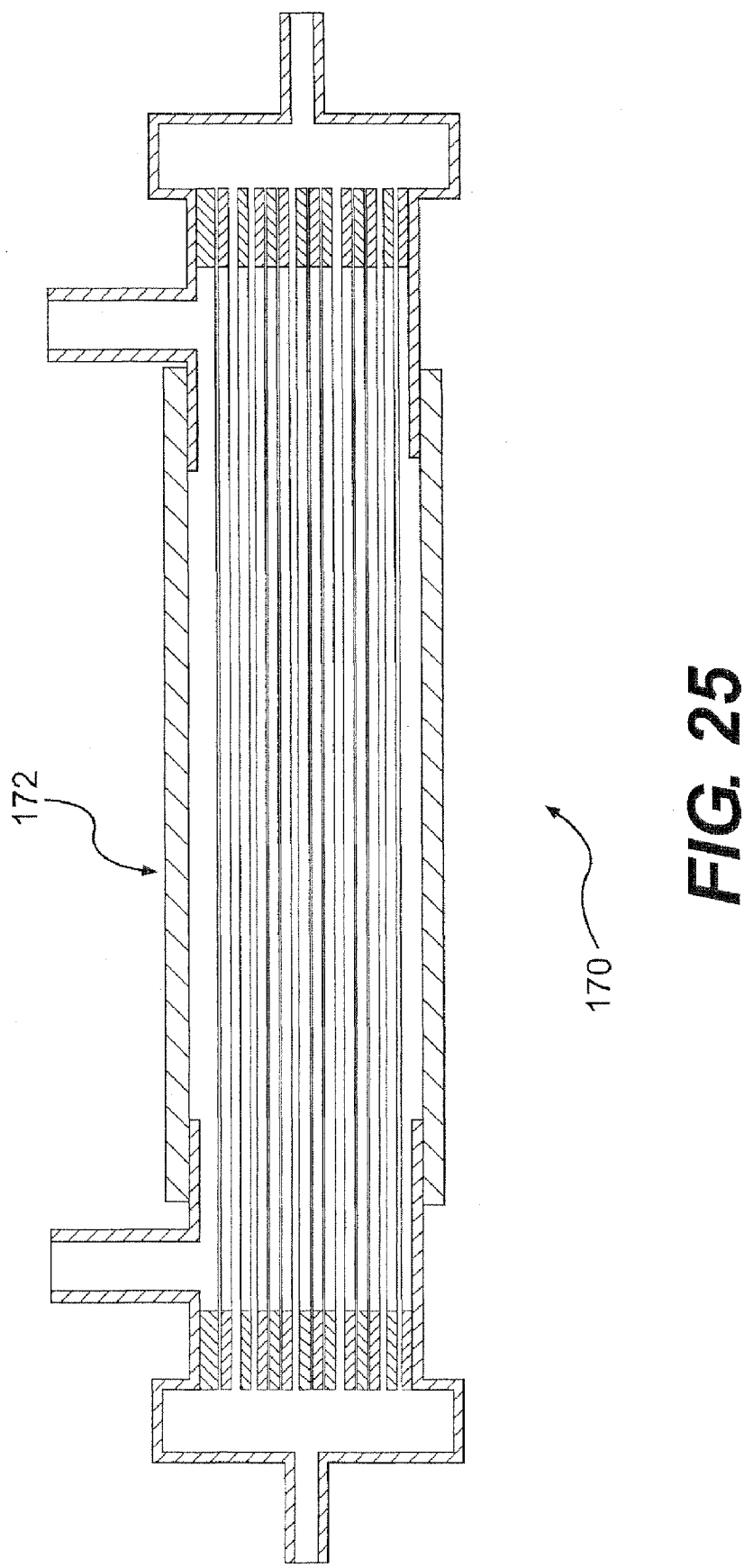
FIG. 25 is a cross-sectional view of a flexible hollow fiber bioreactor according to the present invention.

As shown in FIG. 25, a bioreactor 170 having a flexible outer body 172 allows for physical movement of the cell growth substratum (hollow fibers, membrane or other suitable matrix) when a resultant torqueing or bending moment is applied to the bioreactor ends. Flexible outer body 172 allows for the bioreactor case to be flexed causing fiber movement. This fiber movement enhances the release of cells that have attached to the side of the bioreactor matrix. The cells can then be harvested by flushing either after or during the manipulation. This method can provide increased efficiency of cell harvest at high cell viabilities without the use of chemical or enzymatic release additives.

A bioreactor can be constructed using an outer housing that incorporates a flexible center section. This center section consists of a flexible, non-permeable tubing that allows each end of the bioreactor to be manipulated thus causing movement of the growth matrix. The purpose of this movement is to release the attachment or clumping of cell products on the extra-capillary (EC) side of the fibers. The cell products can then be flushed from the EC via the access port at each end of the bioreactor.

Harvesting cells from a matrix-containing bioreactor such as a hollow fiber bioreactor has been difficult to accomplish. Typically cells are sticky and attach themselves to the fibers or to other cells and form clusters. Rapid flushing of media through the EC to hydraulically force the cells free and into the harvest stream is the most basic method of harvesting cells from the EC space. Typically the quantity of cells harvested is low because the flushing media tends to shunt through the EC and flush cells only from the limited fluid path.

Another method is to physically shake or impact the outer housing to release the cells or clumps of cells. This practice may cause physical damage to the bioreactor or its associated components. Another method includes the use of chemicals to disrupt the adhesion of cells to the fibers or to disrupt the clumps of cells. Adding chemicals to a controlled process may cause adverse effects on cell viability and can introduce an unwanted agent in the down-stream processing.

Figure 26:
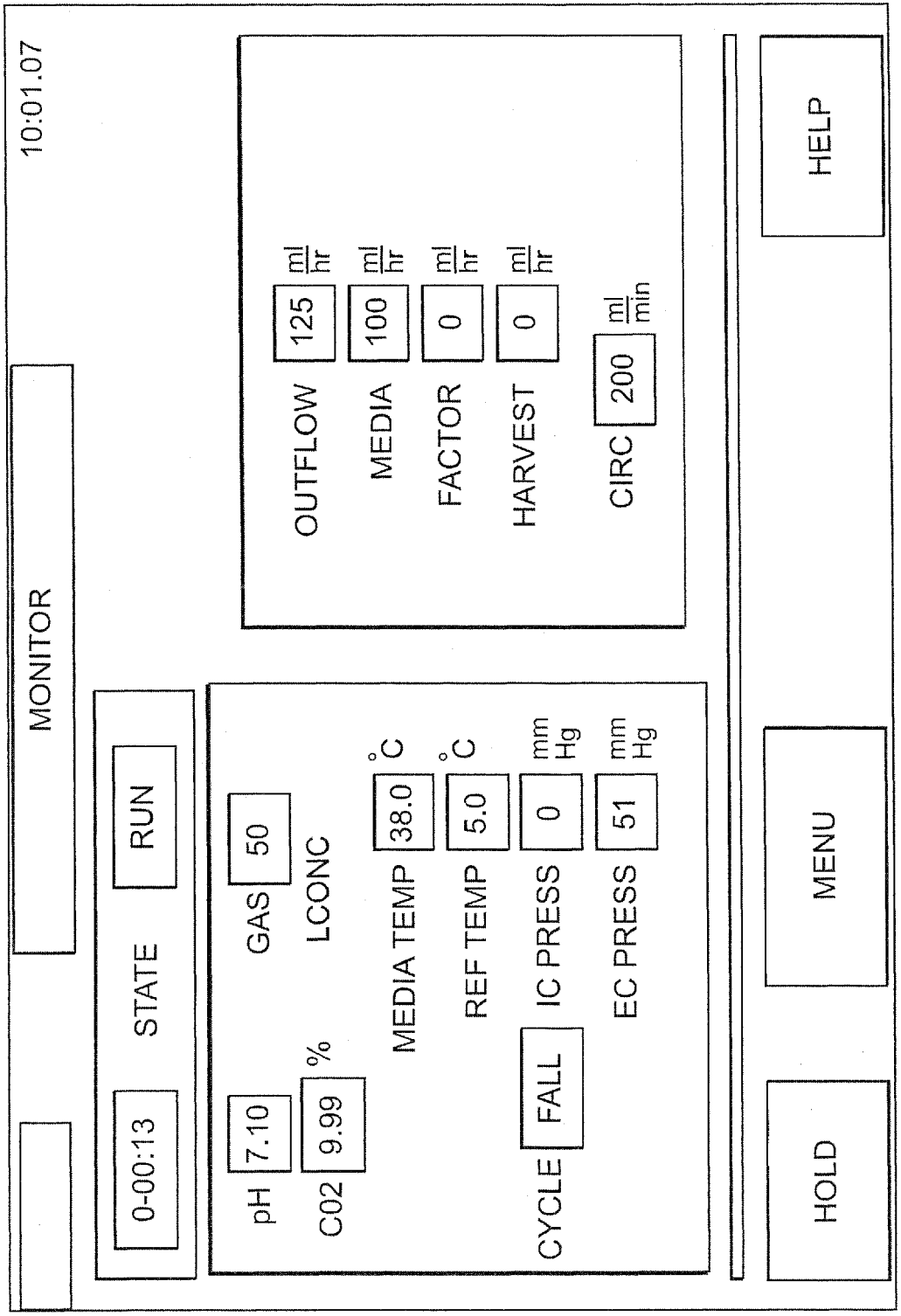
Figure 27:
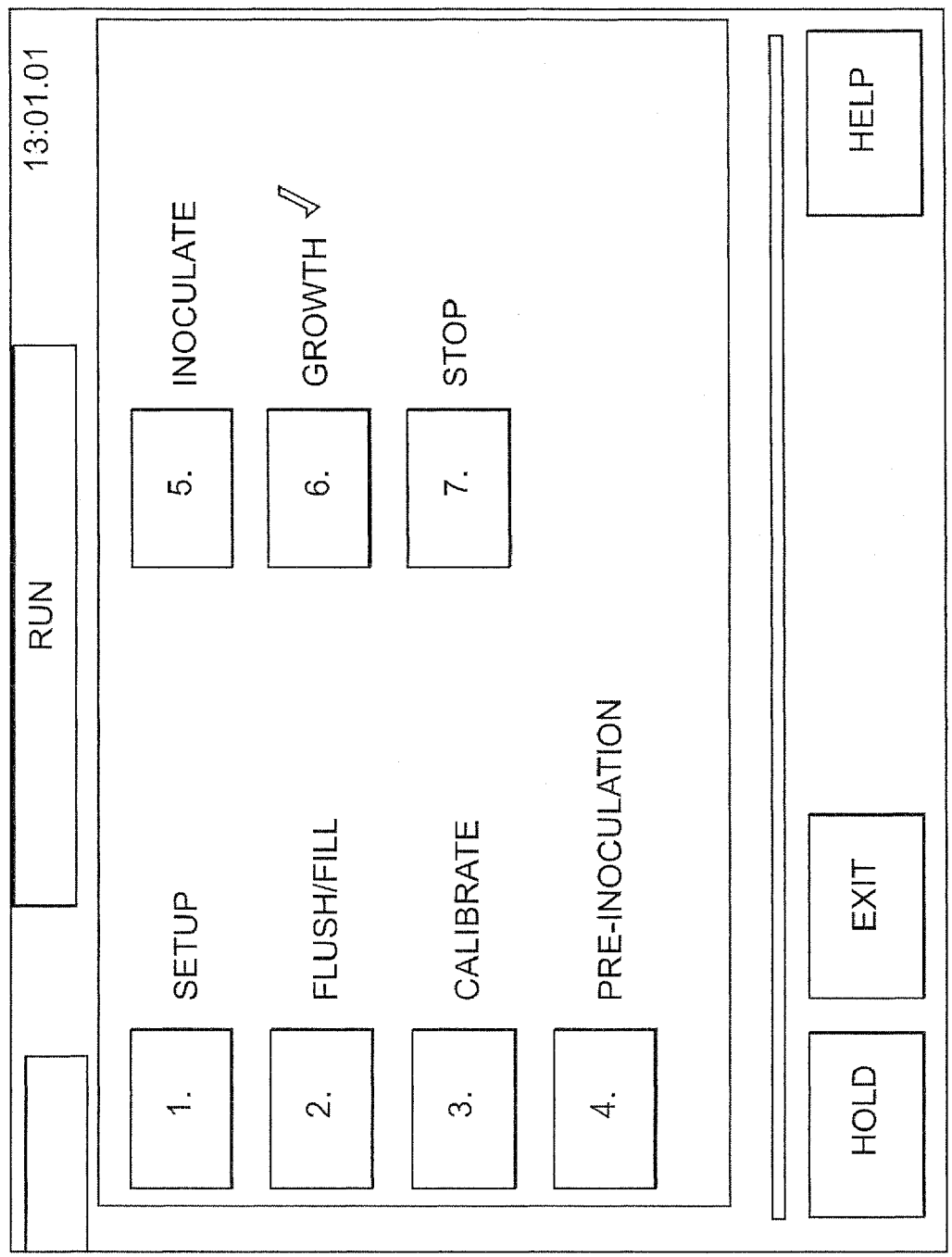
Figure 29:
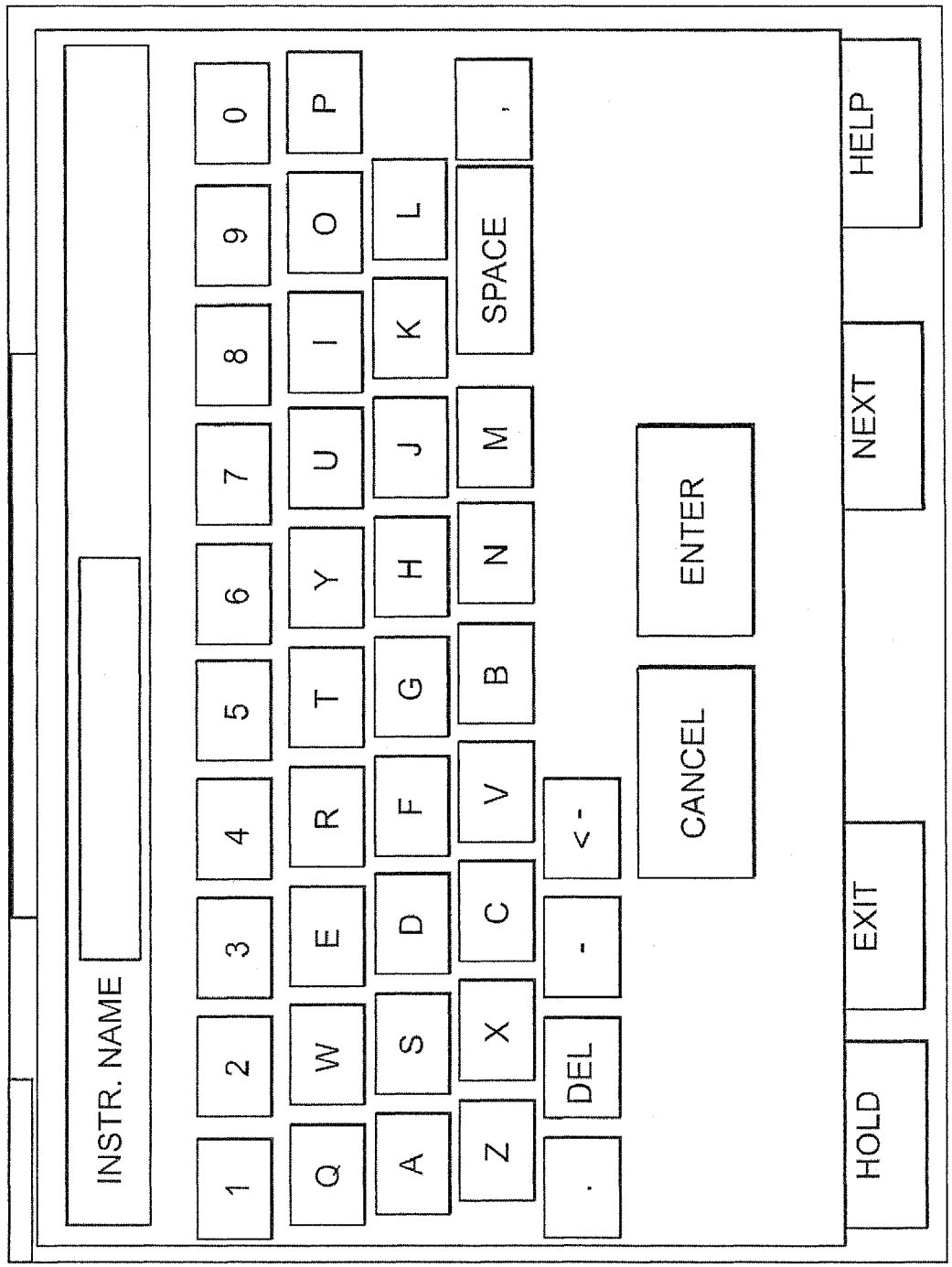
Figure 30:
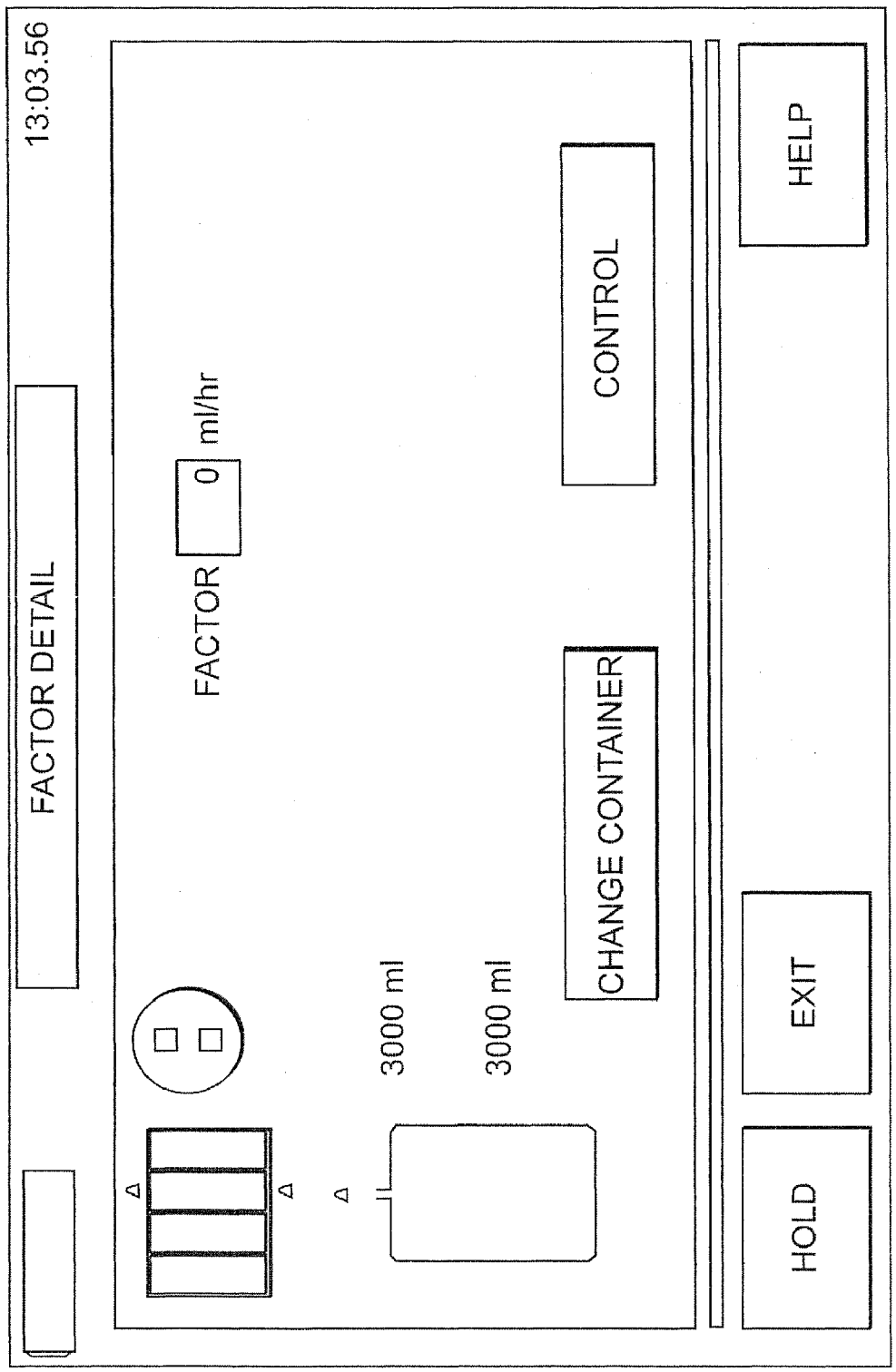
Figure 31:
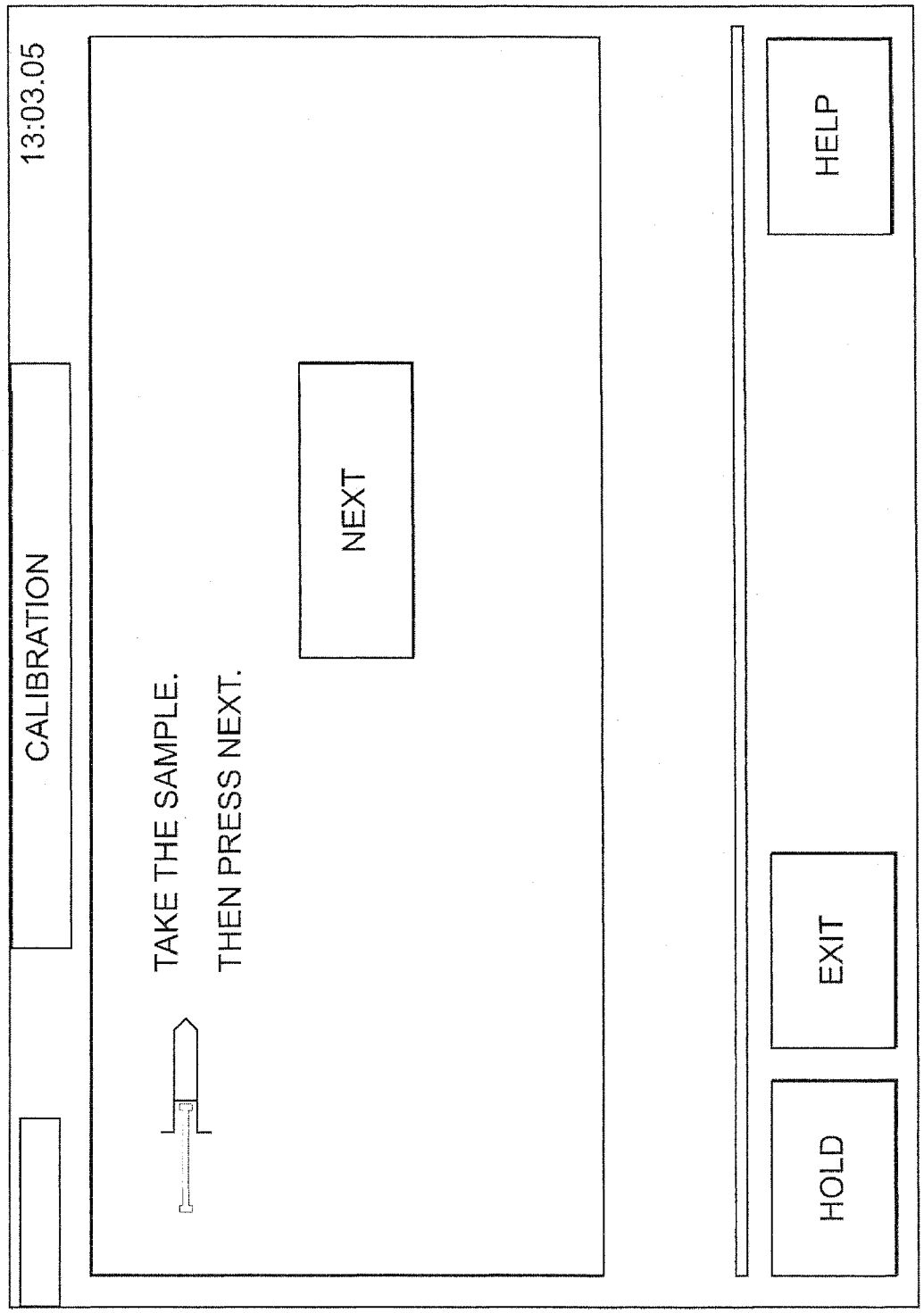

Referring to FIGS. 26-31, various views of touch display screen illustrate the different interactive steps during control process of the system of the present invention. FIG. 26 shows a system overview screen which highlights current conditions. FIG. 27 illustrates a run sequence screen which directs the operator through the culture process. FIG. 28 illustrates log data which the operator can review and which is available to build the batch record. FIG. 29 shows a method for inputting alpha-numeric data. FIGS. 30 and 31 show operator interaction screens to assist in operations (factor addition and pH probe calibration). On line help screens aid the operator for correct operation.

Some examples for which the system of the present invention can be used are:
- The production of monoclonal antibodies from hybridoma cell lines.
- The expansion of autologous patient-derived blood cells including immune cells for therapeutic application.
- The expansion of patient derived somatic cells for subsequent re-infusion back into patients for therapeutic purposes. A specific example already available for therapeutic application in patients is the harvesting and expansion of patient specific cartilage cells (chondrocytes) followed by re-infusion of those cells back into a region containing damaged articular cartilage.
- The expansion of patient derived or generic multipotent cells, including embryonic stem cells, adult stem cells, hematopoeitic stem or progenitor cells, multi or pleuripotent cells derived from cord blood for therapeutic purposes.
- The expansion of somatic or germline cells as in applications 2, 3 and 4 in which the cells have been genetically modified to express novel cellular components or to confer on them other beneficial properties such as novel receptors, altered growth characteristics or genetic features, followed by introduction of the cells into a patient for therapeutic benefit. An example is the expansion of patient specific fibroblasts genetically modified to express growth factors, clotting factors, or other biologically active agents to correct inherited or acquired deficiencies of such factors.

At present, the system of the present invention fully integrates the concept of disposable cultureware into automated process control for maintaining and expanding specialized (autologous or other) cell lines for a duration of any time needed. To accomplish this, the system of the present invention was designed for EC space fluid flow that enhances cell growth in high density perfusion culture, yet remains completely closed and disposable. The integrated pre-assembled cultureware, which consists of all tubing, bioreactor, oxygenator, pH probe, is enclosed in a single unit that easily snaps into the apparatus. In addition to this error-proof, quick-load design, the entire cultureware unit enclosed by the casing becomes the cell culture incubator with temperature control regulated through automated process control of the instrument. Pumps and fluid control valves facilitate disposability and error-proof installation, eliminating the possibility of technician mistakes. Finally, during the course of any culture, the closed system has restricted access except for trained and authorized personnel. Manipulations or sampling, outside of program parameters, require password and bar code access before they can be implemented.

Each unique cell line must be cultured, cell secretions harvested and purified separately. In order to manage a large number of unique cell lines, as for example might be required for the production of large numbers of autologous cell therapeutic products or large numbers of unique monoclonal antibodies, a considerable number of instruments would be needed. Compactness of the design and the amount of ancillary support resources needed become an important facilities issue. Small stirred tank systems require a means of steam generation and distribution (for steam-in-place sterilization) or autoclaves to sterilize the vessels and supporting plumbing. To support a large number of units becomes a logistics problem for the facility. The system of the present invention has no such requirement. Larger scale cell culture is historically done in segregated steps that often require separate types of equipment. Manual handling, storage and tracking is needed for all these steps as the culture expands and product is harvested. The method of the present invention integrates these steps into a continuous, fully integrated sequential process. This eliminates the handling risk and facilitates the data gathering required for thorough documentation of the entire process.

Although the present invention has been described in relation to particular embodiments thereof, many other variations and modifications and other uses will become apparent to those skilled in the art. It is preferred therefore, that the present invention be limited not by the specific disclosure herein, but only by the appended claims.

What is claimed is:

1. A cell culture system for the production of cells and cell derived products comprising:
    a reusable instrumentation base device incorporating hardware to support cell culture growth;
    at least one disposable cell cultureware module removably attachable to said instrumentation base device, said module including a cell growth chamber containing a semi-permeable matrix;
    a media line, for providing cell culture medium to said cell growth chamber;
    a harvest line, for transporting cells or cell derived products from said cell growth chamber and out of said cell cultureware module; and
    an outflow line, for transporting waste or spent media from said cell growth chamber, wherein said instrumentation base device includes a multi-channel peristaltic pump for moving fresh basal media into said at least one cultureware module, wherein said multi-channel peristaltic pump has discrete, variable output control for each channel, and wherein said at least one cultureware module further comprises a pump cassette, wherein said pump cassette is structured to hold multiple peristaltic tubing segments, and wherein said pump cassette is insertable into an interface on said instrumentation base device and allows for said tubing segments to be loaded into said multi-channel peristaltic pump in said instrumentation base device at the same time.

2. The cell culture system of claim 1, wherein said instrumentation device includes a pump, wherein said pump moves growth factor or other supplements into said cell growth chamber and removes product harvest from said cell growth chamber.

3. The cell culture system of claim 1, wherein said instrumentation device includes a plurality of rotary selection valves to control media flow through said at least one cultureware module.

4. The cell culture system of claim 1, wherein said instrumentation device includes a cool storage area for storing growth factor or other supplements and product harvest, and wherein said instrumentation device includes a heating mechanism for heating said cell growth chamber to promote growth and production.

5. The cell culture system of claim 4, wherein said at least one cultureware module includes an inlet and outlet port, said inlet and outlet ports being constructed and arranged to align with air ports of said instrument device such that the heating mechanism forces heated air into said at least one cultureware module from said instrument device.

6. The cell culture system of claim 1, wherein said at least one cultureware module includes a gas blending mechanism in communication with the cell growth chamber, wherein the cell culture system further comprises a pH sensor disposed in said at least one cultureware module to control the pH of the cell culture medium, wherein the gas blending mechanism includes a gas exchange cartridge that provides oxygen and adds or removes carbon dioxide to the medium to support cell metabolism, wherein the gas exchange cartridge has an inlet end and a discharge end, and wherein the cell culture system further comprises a non-invasive carbon dioxide sensor in fluid communication with the discharge end of the gas exchange cartridge for measuring the carbon dioxide level of the cell culture medium by measuring air discharge of the gas exchange cartridge for indirect lactate measurement and control.

7. The cell culture system of claim 1, wherein said at least one cultureware module is pre-sterilized.

8. The cell culture system of claim 1, wherein said instrumentation device includes interface features, wherein said at least one cultureware module includes a plurality of interface features integrated into said at least one cultureware module, and wherein said interface features of said at least one cultureware module are aligned and mate with said interface features of said instrumentation device when said at least one cultureware module is loaded on to said instrumentation device.

9. The cell culture system of claim 1, wherein said at least one cultureware module includes sensors for sensing fluid circulation rate, temperature and pH of the cell culture medium.

10. The cell culture system of claim 1, wherein said cell growth chamber comprises a bioreactor that provides cell space and medium component exchange, and wherein said bioreactor has a flexible outer body.

11. The cell culture system of claim 1, wherein said at least one cultureware module includes a fluid cycling unit disposed therein to cycle and maintain fluid volumes within said cell growth chamber, and wherein said fluid cycling unit includes a first non-rigid reservoir and a second flexible reservoir in fluid communication with the first reservoir to cause elevated pressure in the first reservoir and thereby force fluid through said cell growth chamber.

12. The cell culture system of claim 1, further comprising a plurality of disposable containers for harvest collection and flushing removably connected to said at least one cultureware module.

13. The cell culture system of claim 1, wherein said cell growth chamber is a hollow fiber bioreactor.

14. The cell culture system of claim 1, wherein said instrumentation device further comprises data gathering software in said instrumentation base device that, when used with an information management system, allows for automatic generation of a batch record for each cell culture run.

15. The cell culture system of claim 1, wherein said instrumentation device further comprises a touch screen for user interaction, and wherein said touch screen displays a run sequence screen which directs the operator through a culture process.

16. The cell culture system of claim 11, wherein said cell growth chamber is a hollow fiber bioreactor having an extra-capillary (EC) side and an intra-capillary (IC) side, and wherein the elevated pressure in the first reservoir provides an elevated EC pressure and ultra-filtrative condition that forces fluid across said semi-permeable matrix of said bioreactor, and into an IC circuit.

17. The cell culture system of claim 1, further comprising a factor line for providing growth factors or other supplements to said cell growth chamber.

* * * * *